United States Patent
Ortiz Egea et al.

(10) Patent No.: US 10,996,746 B2
(45) Date of Patent: May 4, 2021

(54) REAL-TIME COMPUTATIONAL SOLUTIONS TO A THREE-DIMENSIONAL EYE TRACKING FRAMEWORK

(71) Applicant: Microsoft Technology Licensing, LLC, Redmond, WA (US)

(72) Inventors: Sergio Ortiz Egea, San Jose, CA (US); Jian Feng Gao, Redmond, WA (US); Alfonsus D. Lunardhi, San Ramon, CA (US); Venkata Satya Raghavendra Bulusu, Fremont, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 63 days.

(21) Appl. No.: 16/414,637

(22) Filed: May 16, 2019

(65) Prior Publication Data

US 2020/0121183 A1   Apr. 23, 2020

Related U.S. Application Data

(63) Continuation-in-part of application No. 16/168,319, filed on Oct. 23, 2018, now Pat. No. 10,718,942.

(51) Int. Cl.
*G06F 3/01*   (2006.01)
*G06F 17/16*   (2006.01)
(Continued)

(52) U.S. Cl.
CPC ......... *G06F 3/013* (2013.01); *G02B 27/0093* (2013.01); *G02B 27/0172* (2013.01);
(Continued)

(58) Field of Classification Search
CPC .......... G06F 3/011; G06F 3/012; G06F 3/013; G02B 27/0093; G02B 27/0172; G02B 27/0179
See application file for complete search history.

(56) References Cited

U.S. PATENT DOCUMENTS 7,091,928 B2   8/2006   Rajasingham
9,075,453 B2   7/2015   Bhaskar et al.
(Continued)

FOREIGN PATENT DOCUMENTS

EP   2893388 A1   7/2015
WO   2013168171 A1   11/2013
(Continued)

OTHER PUBLICATIONS

"Non-Final Office Action Issued in U.S. Appl. No. 16/414,654", dated Apr. 27, 2020, 11 Pages.
(Continued)

*Primary Examiner* — Lisa S Landis
(74) *Attorney, Agent, or Firm* — Newport IP, LLC; Mike R. Cicero

(57) ABSTRACT

Techniques for implementing eye tracking using various real-time computational solutions to a three-dimensional eye tracking framework. An exemplary eye tracking system for a NED device includes sensors that are directed toward and angularly offset from a user's eyes in a manner that causes circular features (e.g., irises and/or pupils) of the user's eyes to appear elliptical within sensor planes of the individual sensors. An iris and/or pupil of an eye will appear circular when the eye is looked at straight on (i.e., perpendicular to an optical axis of the eye's lens) but elliptical when observed from an angular offset. The eye tracking systems and methods disclosed herein exploit these principles to track movements of the user's eyes with a higher degree of accuracy than conventional eye tracking systems.

20 Claims, 17 Drawing Sheets

(51) Int. Cl.
    *G02B 27/00*     (2006.01)
    *G02B 27/01*     (2006.01)
    *A61B 3/11*     (2006.01)
    *A61B 3/00*     (2006.01)

(52) U.S. Cl.
    CPC ............ *G06F 17/16* (2013.01); *A61B 3/0025* (2013.01); *A61B 3/111* (2013.01)

(56) References Cited

U.S. PATENT DOCUMENTS

| | | | |
|---|---|---|---|
| 9,299,183 | B2 | 3/2016 | Vesely |
| 9,335,547 | B2 | 5/2016 | Takano et al. |
| 9,507,426 | B2 | 11/2016 | Raffle |
| 9,514,538 | B2 | 12/2016 | Ebisawa |
| 9,766,463 | B2 | 9/2017 | Border et al. |
| 9,952,665 | B2 | 4/2018 | Di Censo et al. |
| 10,067,561 | B2 | 9/2018 | San Agustin Lopez |
| 2006/0250322 | A1 | 11/2006 | Hall et al. |
| 2013/0050432 | A1 | 2/2013 | Perez et al. |
| 2013/0050833 | A1 | 2/2013 | Lewis et al. |
| 2013/0083003 | A1* | 4/2013 | Perez ............... A63F 13/422 345/419 |
| 2013/0241805 | A1 | 9/2013 | Gomez |
| 2014/0285404 | A1 | 9/2014 | Takano et al. |
| 2015/0097772 | A1 | 4/2015 | Starner |
| 2015/0262424 | A1 | 9/2015 | Tabaka et al. |
| 2015/0301599 | A1 | 10/2015 | Miller |
| 2015/0309568 | A1 | 10/2015 | Miki |
| 2016/0025971 | A1 | 1/2016 | Crow et al. |
| 2016/0203359 | A1 | 7/2016 | Von Und Zu Liechtenstein |
| 2016/0225153 | A1 | 8/2016 | Kim |
| 2017/0069135 | A1 | 3/2017 | Komaki et al. |
| 2017/0108697 | A1 | 4/2017 | El-ghoroury et al. |
| 2017/0123492 | A1 | 5/2017 | Marggraff et al. |
| 2018/0300952 | A1 | 10/2018 | Evans et al. |
| 2018/0350145 | A1 | 12/2018 | Byl et al. |
| 2020/0125166 | A1 | 4/2020 | Ortiz egea et al. |

FOREIGN PATENT DOCUMENTS

| | | |
|---|---|---|
| WO | 2014205422 A2 | 12/2014 |
| WO | 2015013022 A1 | 1/2015 |

OTHER PUBLICATIONS

"Non Final Office Action Issued in U.S. Appl. No. 16/168,319", dated Oct. 17, 2019, 11 Pages.

"Non Final Office Action Issued in U.S. Appl. No. 16/383,474", dated Apr. 9, 2020, 15 Pages.

"International Search Report and Written Opinion Issued in PCT Application No. PCT/US2019/055280", dated Feb. 27, 2020, 10 Pages.

"Non Final Office Action Issued in U.S. Appl. No. 16/383,498", dated Apr. 15, 2020, 20 Pages.

"International Search Report and Written Opinion Issued in PCT Application No. PCT/US19/054911", dated Jan. 31, 2020, 10 Pages.

"International Search Report and Written Opinion Issued in PCT Application No. PCT/US19/054912", dated Feb. 6, 2020, 11 Pages.

"International Search Report and Written Opinion Issued in PCT Application No. PCT/US19/055279", dated Jan. 28, 2020, 12 Pages.

"International Search Report and Written Opinion Issued in PCT Application No. PCT/US19/055749", dated Feb. 4, 2020, 12 Pages.

* cited by examiner

REAL-TIME COMPUTATIONAL SOLUTIONS TO A THREE-DIMENSIONAL EYE TRACKING FRAMEWORK

PRIORITY APPLICATION

This U.S. non-provisional application is a continuation in part application that claims benefit of and priority to U.S. Non-Provisional application Ser. No. 16/168,319, filed Oct. 23, 2018, entitled EYE TRACKING SYSTEMS AND METHODS FOR NEAR-EYE-DISPLAY (NED) DEVICES, the entire contents of which are incorporated herein by reference.

BACKGROUND

Near-Eye-Display (NED) systems superimpose computer-generated images ("CG images") over a user's view of a real-world environment. For example, a NED system may generate composite views to enable a user to visually perceive a CG image superimposed over a physical object that exists within the real-world environment. In some instances, a user's experience is highly dependent on the NED system accurately tracking the user's eye movements. For example, in some instances the NED system may track an interpupillary distance (IPD) of the user. One reason for tracking IPD is so that CG images can be rendered at a suitable separation within the user's field of view. Additionally, or alternatively, the NED system may track a depth at which the user is focusing within the real-world environment. One reason for tracking the user's focal depth (e.g., accommodation plane) is because the user may experience motion sickness or vertigo if CG images are rendered at a depth that is different (i.e., closer to/farther from the user) than that which the user is focusing.

Some conventional eye tracking systems illuminate the user's eyes with near infrared light and then track the user's eye movements by observing reflective patterns that are formed from the near infrared light. For example, upon being illuminated with near infrared light, the eyes may form one or more first Purkinje reflections (e.g., "glints") that are distributed around the iris. Conventional eye tracking systems track eye movements (e.g., the user's gaze direction) by analyzing the location(s) of these Purkinje reflections with respect to the center of the pupil.

In some instances, convention eye tracking systems estimate the user's line of sight by observing the Purkinje reflections with the addition of head tracking information. Unfortunately, even an accurate estimation of the user's line of sight may be insufficient to accurately determine the depth at which the user is focusing within the real-world environment. This is because the user's line of sight and the user's visual axis (which actually propagates to the user's fovea) only converge at a single depth plane.

It is with respect to these and other considerations that the disclosure made herein is presented.

SUMMARY

Technologies described herein provide eye tracking systems and methods implementing eye tracking systems and methods for Near-Eye-Display (NED) devices using various real-time computational solutions to a three-dimensional eye tracking framework. Complete computational solutions to the 3D eye tracking framework described below may be accomplished in a variety of forms. Although some such complete computational solutions are described herein, others are contemplated and within the scope of the present disclosure. With respect to the 3D eye tracking framework, an exemplary eye tracking system for a NED device includes sensors that are directed toward and angularly offset from a user's eyes in a manner that causes circular features (e.g., irises and/or pupils) of the user's eyes to appear elliptical within sensor planes of the individual sensors. For example, it can be appreciated that an iris and/or pupil of an eye will appear circular when the eye is looked at straight on (i.e., perpendicular to an optical axis of the eye's lens) but elliptical when observed from an angular offset. The eye tracking systems and methods disclosed herein exploit these principles to track movements of the user's eyes with a higher degree of accuracy than conventional eye tracking systems.

Various embodiments disclosed herein track the user's interpupillary distance (IPD) in real time while the NED device is operating—rather than merely determining the user's IPD at predetermined intervals as conventional eye tracking systems do. Additionally, or alternatively, various embodiments disclosed herein track the user's visual axes—rather than merely tracking the user's optical axis and/or line of sight as conventional eye tracking systems do. Then, by determining a vergence in space between the visual axes for each of the user's two eyes, such embodiments calculate the depth in space at which the user is focused with a significantly higher degree of accuracy than conventional eye tracking systems. Accordingly, the disclosed eye tracking systems and methods represents a substantial advance toward preventing a user of a NED device from experiencing motion sickness or vertigo due to CG images being generated in front of or behind the user's accommodation plane (e.g., focal plane).

In an exemplary embodiment, an eye tracking system includes one or more sensors that generate eye tracking data associated with one or more substantially circular features of one or both of a user's eyes. Exemplary such "substantially" circular features include pupils and irises which are generally very close to circular and, therefore, may be modeled as perfect circles for purposes of the calculations described herein. The individual sensors have corresponding sensor planes that are angularly skewed with respect to the planes on which the circular features reside (e.g., an Iris-Pupil Plane). Based on the eye tracking data, the eye tracking system determines ellipse parameters for ellipses that result from these sensor planes being angularly skewed from the Iris-Pupil Planes. In some embodiments, the eye tracking system may track only one of the user's eyes. In other embodiments, the eye tracking system may track both of the user's eyes. In embodiments that track both eyes, the eye tracking system may determine ellipse parameters that define: (i) first ellipses that correspond to projections of an iris and/or pupil of a right eye onto a first sensor plane; and (ii) second ellipses that correspond to projections of an iris and/or pupil of a left eye onto a second sensor plane. The projections of each of the iris(es) and/or pupil(s) onto the corresponding sensor plane(s) may in some embodiments pass through a predetermined point such as, for example, an entrance pupil of each corresponding sensor.

Based on the ellipse parameters, the eye tracking system may then generate propagation data that defines three-dimensional (3D) propagations of the ellipses. The 3D propagation data may define a series of lines (e.g., rays) that extend from individual ellipses that are detected on the sensor plane. For example, individual lines of the series of lines may begin on the sensor plane at individual points along a perimeter of a detected ellipse. The individual lines may all commonly propagate from the sensor plane through a predetermined point toward the user's eyes. In some implementations, the predetermined point through which all lines of a particular 3D propagation pass is an entrance pupil of a corresponding sensor. Since all of the lines of these 3D propagations extend from the ellipse through the predetermined point, the 3D propagations may be graphically represented as an elliptic cone that extends from the predetermined point toward the eye.

The eye tracking system may utilize the propagation data to determine pupil orientation parameters that define various characteristics of the user's eye(s). Exemplary pupil orientation parameters may define optical axes for one or both of the user's eyes (e.g., an axis of an eye lens), visual axes for one or both of the user's eyes (e.g. axes that extend from the fovea through the lens and into the real-world environment), rotational angles of the user's eyes (e.g. an angle of rotation between a semi-axis of an ellipse and a horizontal axes of the sensor), Iris-Pupil Planes of the user's eyes (e.g. a plane on which the pupil resides), center points for the user's eyes (e.g., a point at which the optical axis (or alternatively the visual axis) intersects the Iris-Pupil plane). Additionally, or alternatively, the pupil orientation parameters may define various other characteristics of the user's eyes.

As described in detail below, the eye tracking system may utilize the pupil orientation parameters to continually determine of a current (e.g., real time) IPD for a user, i.e. while the NED device is operating. For example, the eye tracking system may dynamically track the center points for each of the user's two eyes and continually calculate and re-calculate the user's interpupillary distance in near real time. Additionally, or alternatively, the eye tracking system may utilize the pupil orientation parameters to determine a vergence of two visual axes (which are different than the optical axis) of the user. For example, the eye tracking system may dynamically track the visual axis of each of the user's two eyes and continually calculate a location in space at which the distance between these two visual axes is the smallest. In various implementations, the visual axes are determined based on visual axis offset data that indicates at least an angular relationship between the optical axis and the visual axis. As described in detail below, this visual axis offset data may be specifically custom to a particular user and may be determined through a user-specific calibration process. It can be appreciated that although vergence is generally understood as the "point" at which the user's two visual axis intersect, in a practical sense these axes rarely mathematically intersect but rather simply become the closest at the user's accommodation plane. Thus, as described herein the vergence of the visual axes may be determined by calculating a point in space at which the separation between the two visual axes is the least (i.e., wherever the two axes become closest together).

In some embodiments, the pupil orientation parameters may be determined by analyzing the propagation data with respect to an ocular rotation model to calculate an orientation of the Iris-pupil plane for an eye, a distance from a predetermined point of the sensor to a center of an entrance pupil of the eye, and/or a radius of the pupil of the eye. The ocular rotation model may be usable to model rotation of a circular feature of an eye around that eye's center of rotation. For example, the ocular rotation model may be (or be based on) an equation that defines coordinates for a circle of a particular radius as that circle is rotated around the center of an eye. It can be appreciated that a circle of a specific radius will mathematically match the "elliptical" 3D propagations only at a single plane. Therefore, utilizing various error minimization algorithms to analyze the propagation data with respect to the ocular rotation model may yield the Iris-Pupil plane's specific location in space and the circular pupil's specific location and rotation thereon. Although some specific error minimization algorithms are described herein, such descriptions are provided for exemplary purposes only and other error minimization algorithms may also be used.

The foregoing description provides a novel mathematical framework for enabling a variety of eye tracking techniques. As described in detail above, principle benefits of the novel mathematical framework include that the techniques it enables needn't rely on dedicated light sources to illuminate the eyes (e.g., to form Purkinje reflections from near infrared light) as many conventional eye tracking systems do to observe the eye orientation. Rather, under even dimly lighted environmental circumstances, the eye tracking techniques described herein may deploy cameras to observe a user's eyes under ambient light alone. Then, based on eye tracking data generated by the cameras and a presumption of the pupils and/or irises being substantially circular features, the techniques described herein determine ellipse parameters associated with an angular offset of the sensor planes (e.g., of the cameras) with respect to the Iris-Pupil Planes. Ultimately, the ellipse parameters may be utilized to determine various characteristics of the user's eyes such as, for example, directions of optical axes (e.g., an axis of an eye lens), directions of visual axes (e.g. axes that extend from the fovea through the lens and into the real-world environment), rotational angles (e.g. an angle of rotation between a semi-axis of an ellipse and a horizontal axes of the sensor), Iris-Pupil Planes (e.g. a plane on which the pupil resides), and/or center points for the user's eyes (e.g., a point at which the optical axis (or alternatively the visual axis) intersects the Iris-Pupil plane).

It will be appreciated by one skilled in the art that complete solutions the novel mathematical framework described above may be accomplished in a variety of forms. Various individual ones of these forms may rely upon a variety of assumptions. As described below, assumptions may be selected in order to simply and/or enable calculations of a complete solution to the mathematical framework described above. As a specific example, an assumption as to the size (e.g., diameter or radius) of an iris may be made to simply a complete solution to obtaining eye tracking information—thereby reducing the computational resources required to perform eye tracking techniques. As further described below, in various implementations certain assumptions may be made or not to achieve a desired level of accuracy of the resulting eye tracking information. For example, in some instances certain assumptions may simply the calculations to a complete solution of the mathematical framework at the expense of some level of accuracy. Various individual ones of the various forms of a complete solution may utilize a variety of equations including, but not limited to, those equations provided and described below.

It should be appreciated that any reference to "first," "second," etc. items and/or abstract concepts within the Summary and/or Detailed Description is not intended to and should not be construed to necessarily correspond to any reference of "first," "second," etc. elements of the claims. In particular, within the Summary and/or Detailed Description, items and/or abstract concepts such as, for example, three-dimensional (3D) propagations and/or circular features of eyes and/or sensor entrance pupils may be distinguished by numerical designations without such designations corresponding to the claims or even other paragraphs of the Summary and/or Detailed Description. For example, any designation of a "first 3D propagation" and "second 3D propagation" of the eye tracking system within any specific paragraph of this the Summary and/or Detailed Description is used solely to distinguish two different 3D propagations of the eye tracking system within that specific paragraph—not any other paragraph and particularly not the claims.

These and various other features will be apparent from a reading of the following Detailed Description and a review of the associated drawings. This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DRAWINGS

The Detailed Description is described with reference to the accompanying figures. In the figures, the left-most digit(s) of a reference number identifies the figure in which the reference number first appears. The same reference numbers in different figures indicate similar or identical items. References made to individual items of a plurality of items can use a reference number with another number included within a parenthetical (and/or a letter without a parenthetical) to refer to each individual item. Generic references to the items may use the specific reference number without the sequence of letters.

DETAILED DESCRIPTION

Figure 1:
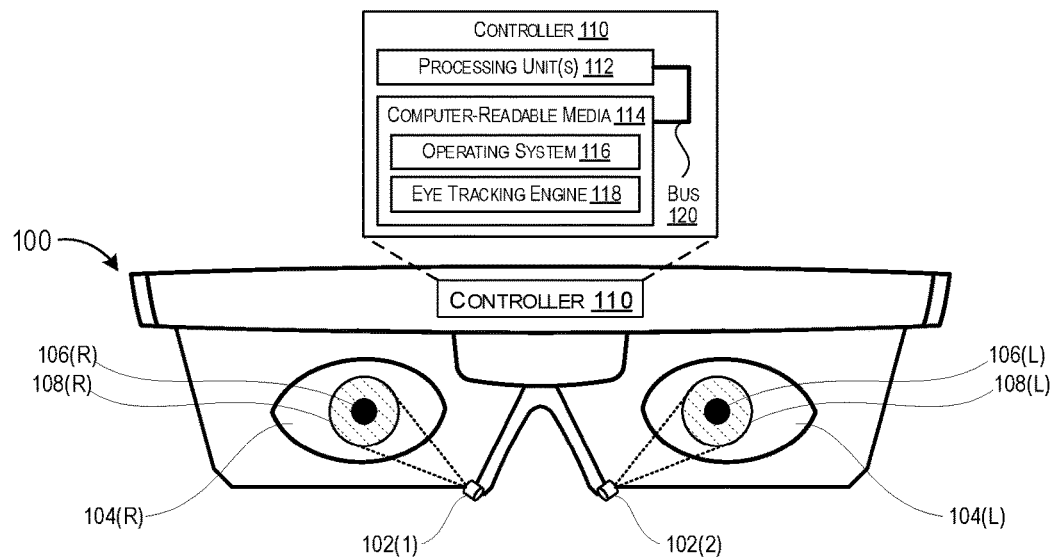
FIG. 1 illustrates an exemplary hardware layout for a Near-Eye-Display (NED) device that is configured to implement the methods described herein.

The following Detailed Description describes technologies for implementing eye tracking systems and methods for Near-Eye-Display (NED) devices using various real-time computational solutions to a three-dimensional eye tracking framework. Complete computational solutions to the 3D eye tracking framework described below may be accomplished in a variety of forms. Although some such complete computational solutions are described herein, others are contemplated and within the scope of the present disclosure. With respect to the 3D eye tracking framework, an exemplary eye tracking system for a NED device includes sensors that are directed toward and angularly offset from a user's eyes in a manner that causes circular features (e.g., irises and/or pupils) of the user's eyes to appear elliptical within sensor planes of the individual sensors. For example, it can be appreciated that an iris and/or pupil of an eye will appear circular when the eye is looked at straight on (i.e., perpendicular to an optical axis of the eye's lens) but elliptical when observed from an angular offset. The eye tracking systems and methods disclosed herein exploit these principles to track movements of the user's eyes with a higher degree of accuracy than conventional eye tracking systems.

As described in more detail below, various embodiments track the user's visual axes—rather than merely tracking the user's optical axis and/or line of sight as conventional eye tracking systems do. It will be appreciated from the following discussion that determining a vergence in space between the visual axes for each of the user's two eyes provides substantially more actual calculations of the depth in space at which the user is focused than is currently achievable by conventional eye tracking systems. The disclosed eye tracking systems and methods therefore represent a substantial advance toward preventing a user of a NED device from experiencing motion sickness or vertigo due to CG images being generated in front of or behind the user's current (e.g., real time) accommodation plane (e.g., focal plane).

Aspects of the techniques described herein are primarily described in the context of the sensors being cameras that contain one or more lenses that define an entrance pupil that is disposed in front of an image-sensor (e.g., a CMOS sensor). In such embodiments, the image sensor may generate eye tracking data in the form of pixel data that defines images of the user's eyes. While the disclosed techniques are not necessarily limited to using cameras, an appreciation of various aspects of the invention is best gained through a discussion of example in such a context. However, any type of sensor that is suitable for observing a shape and/or orientation of the iris and/or pupil of the user's eye shall be considered variations of the techniques described herein. For example, it will be appreciated that various forms of lenses sensors may also be suitable for implementing the techniques described herein.

Turning now to FIG. 1, illustrated is an exemplary hardware layout for a Near-Eye-Display (NED) device 100 that is configured to implement the methods described herein. In the exemplary hardware layout the NED device 100 includes a pair of sensors 102 that are each directed toward a corresponding eye 104 of a user. More specifically, the illustrated NED device 100 includes a first sensor 102(1) that is angularly offset from and directed toward a right eye 104(R) and also a second sensor 102(1) that is angularly offset from and directed toward a left eye 104(L). The right eye 104(R) includes a corresponding pupil 106(R) and a corresponding iris 108(R). The left eye 104(L) includes a corresponding pupil 106(L) and a corresponding iris 108(L). The sensors 102 can be in any suitable form such as, for example, a non-contact sensor configured to use optical-based tracking (e.g. video camera based and/or some other specially designed optical-sensor-based eye tracking technique) to monitor the one or more physical characteristics of the user's eyes. Exemplary physical characteristics include, but are not limited to, pupil size, a rate of change of pupil size, gaze direction, and/or a rate of change to a gaze direction.

FIG. 1 is illustrated from a perspective that is directly in front of the optical axes of the eyes 104 so that the pupils 106 and irises 108 appear perfectly circular. It will be appreciated by one skilled in the art that in humans (and many other vertebrates for that matter) the pupils 106 and irises 108 of the eyes 104 are almost perfect circles. Therefore, in various calculations described below, the pupils 106 and/or irises 108 are mathematically modeled as and/or presumed to be perfectly circular in shape. From the perspective of the individual sensors 102, however, the pupils 106 and irises 108 of the eyes 104 appear to be elliptical as described herein. This is because the sensors 102 are angularly offset from the eyes 104 in the sense that the optical axis of each individual sensor 102 is not parallel to the optical axis of the eye 104 it is tracking. The position of the sensors 102 shown in FIG. 1 is for illustrative purposes only. It will be appreciated that the techniques described herein can be performed with the sensors 102 being located in a variety of positions with respect to the eyes. As a specific but nonlimiting example, the sensors could be embedded within a lens or other substrate directly in front of the eyes.

In the illustrated embodiment, the NED device 100 further includes a controller 110 that is configured to implement the various operations of the methods described herein. The controller 110 may be communicatively coupled to the sensors 102 to receive eye tracking data that is generated by the sensors 102 in association with the circular features of the eyes. The controller 110 may further be communicatively coupled to other componentry of the NED display device 100. The controller 110 includes one or more logic devices and one or more computer memory devices storing instructions executable by the logic device(s) to deploy functionalities described herein with relation to the NED device 100. The controller 116 can comprise one or more processing units 112, one or more computer-readable media 114 for storing an operating system and data such as, for example, eye tracking data, visual axis offset data, application data, etc. The computer-readable media 114 may further include an eye tracking engine (e.g., module) configured to receive the eye tracking data from the sensor 102 and, based thereon, determine one or more physical characteristics of the user's eyes using the methods and techniques described herein. The components of the NED device 100 are operatively connected, for example, via a bus 120, which can include one or more of a system bus, a data bus, an address bus, a PCI bus, a Mini-PCI bus, and any variety of local, peripheral, and/or independent buses.

The processing unit(s) 112, can represent, for example, a CPU-type processing unit, a GPU-type processing unit, a field-programmable gate array (FPGA), another class of digital signal processor (DSP), or other hardware logic components that may, in some instances, be driven by a CPU. For example, and without limitation, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), etc.

As used herein, computer-readable media, such as computer-readable media 114, can store instructions executable by the processing unit(s). Computer-readable media can also store instructions executable by external processing units such as by an external CPU, an external GPU, and/or executable by an external accelerator, such as an FPGA type accelerator, a DSP type accelerator, or any other internal or external accelerator. In various examples, at least one CPU, GPU, and/or accelerator is incorporated in a computing device, while in some examples one or more of a CPU, GPU, and/or accelerator is external to a computing device.

Computer-readable media can include computer storage media and/or communication media. Computer storage media can include one or more of volatile memory, non-volatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including but not limited to random access memory (RAM), static random-access memory (SRAM), dynamic random-access memory (DRAM), phase change memory (PCM), read-only memory (ROM), erasable programmable read-only memory (EPROM), electrically erasable programmable read-only memory (EEPROM), flash memory, rotating media, optical cards or other optical storage media, magnetic storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In contrast to computer storage media, communication media can embody computer-readable instructions, data structures, program modules, or other data in a modulated data signal, such as a carrier wave, or other transmission mechanism. As defined herein, computer storage media does not include communication media. That is, computer storage media does not include communications media consisting solely of a modulated data signal, a carrier wave, or a propagated signal, per se.

The NED device 100 may further include various other components, for example speakers, microphones, accelerometers, gyroscopes, magnetometers, temperature sensors, touch sensors, biometric sensors, other image sensors, energy-storage components (e.g. battery), a communication facility, a GPS receiver, etc.

Figure 2:
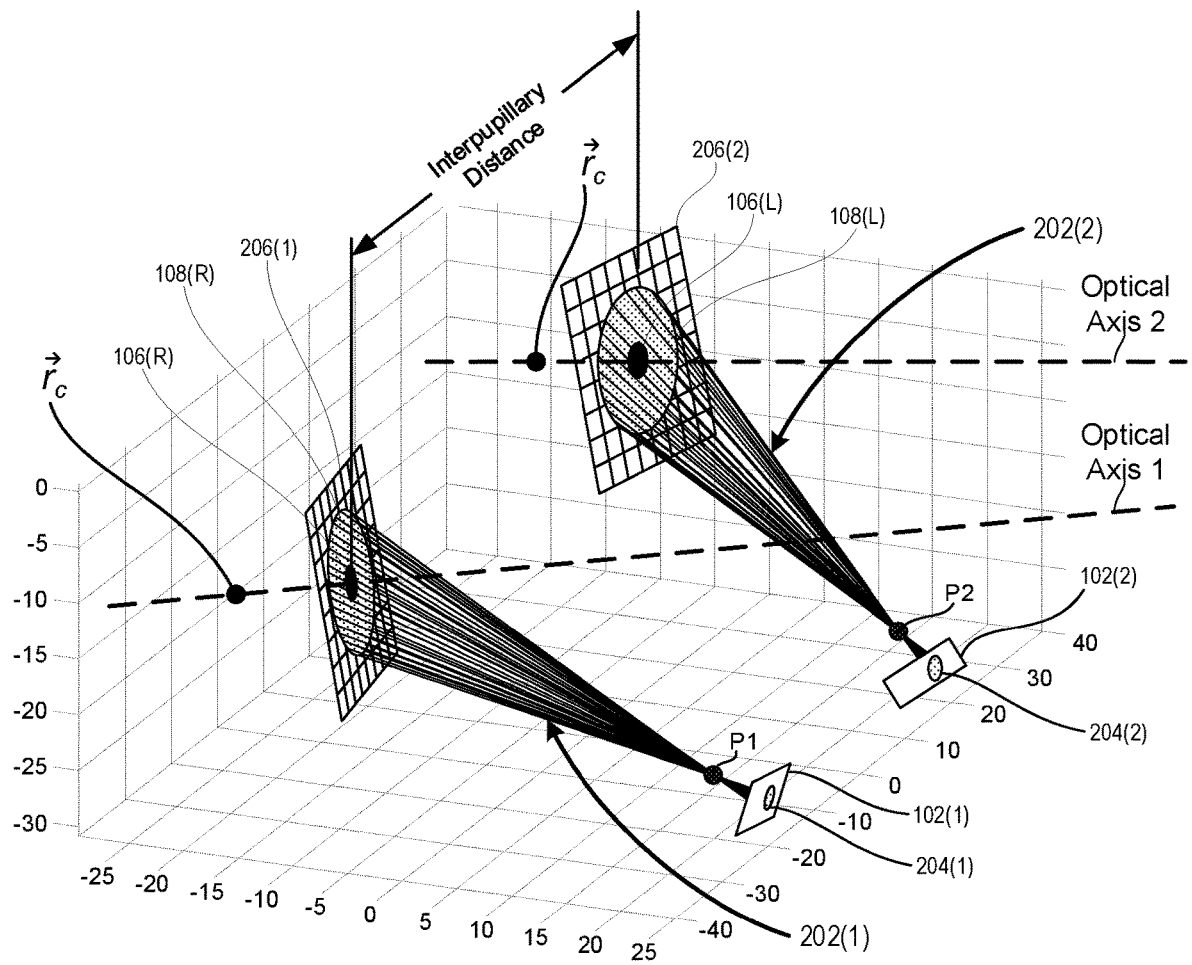
FIG. 2 illustrates a pair of three-dimensional (3D) propagations that extend from ellipses that result from circular features of user's eyes being projected into the sensors.

Turning now to FIG. 2, illustrated is a pair of three-dimensional (3D) propagations 202 that extend from ellipses 204 that result from circular features (e.g., pupils 106 and/or irises 108) of user's eyes 104 being projected into the sensors 102. As illustrated, a first 3D propagation 202(1) extends from a first ellipse 204(1), which is detected at the first sensor 102(1), through a first point P1. As further illustrated, a second 3D propagation 202(2) extends from a second ellipse 204(2), which is detected at the second sensor 102(2), through a second point P2. Each of the 3D propagations 202 extend toward a corresponding Iris-Pupil plane 206 that is angularly offset with respect to the sensors 102. The angularly offset nature of the Iris-Pupil planes 206 results in the pupils 106 and irises 108 appearing elliptical from the perspectives of the sensors 102.

As illustrated, each of the individual 3D propagations 202 may include a series of lines that extend from a perimeter of a corresponding individual ellipse 204 through a corresponding predetermined point and, ultimately, to the perimeter of a circular feature (e.g., pupil 106 or iris 108) that resides within a corresponding Iris-Pupil plane 206. The predetermined points (e.g., P1 and P2) may correspond to specific points in space that are measurable in relation to corresponding sensors 102. For example, the first predetermined point P1 may correspond to a center of an entrance pupil of the first sensor 102(1) whereas the second predetermined point P2 may correspond to a center of an entrance pupil of the second sensor 102(2). Thus, it can be appreciated that P1 may correspond to a point in space at which light rays cross prior to forming an image within the first sensor 102(1) and that P2 may correspond to a point in space at which light rays cross prior to forming an image within the second sensor 102(2).

As described in more detail below, these 3D propagations 202 may be used to determine pupil orientation parameters that define various characteristics of the user's pupil(s) 106. For example, it can be appreciated that the 3D propagations 202 can be mathematically modeled as elliptical cones. This is because individual ones of the 3D propagations 202 originate at a corresponding ellipse 204 and pass through a singular point. It can further be appreciated that a cross-section of an elliptical cone will be circular in shape if that cross-section is taken at a specific orientation. Thus, by using the mathematical assumption that the pupils 106 and irises 108 are circular in shape, the 3D propagations 202 may enable a determination of the specific orientation of the Iris-Pupil planes 206. Additionally, as described in more detail below, performing various error minimization techniques of the 3D propagations with respect to an ocular rotation model may further enable a determination of the center points of the pupils 106. It can be appreciated that once the location in space of the center point of a pupil 106 and an orientation of an Iris-Pupil plane 206 is known for a particular eye, the optical axis (illustrated as dashed lines for each eye) for that particular eye is also known.

Figure 3:
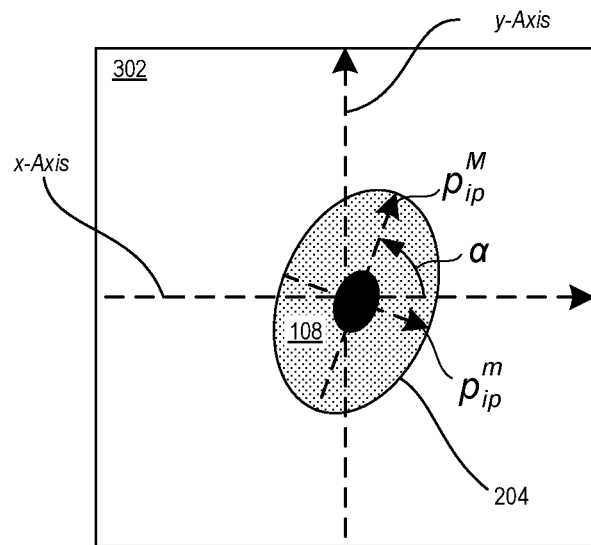
FIG. 3 illustrates in an exemplary ellipse that is being projected onto a sensor plane within a sensor that is angularly skewed with respect to the Iris-Pupil plane (not shown in FIG. 3) so that circular features on the Iris-Pupil plane appear elliptical on the sensor plane.

Turning now to FIG. 3, illustrated in an exemplary ellipse 204 that is projected from a circular feature of an eye 104 (e.g., an Iris 108) onto a sensor plane 302 of a sensor 102. The sensor plane 302 may correspond to a substantially planar surface within the sensor 102 that is angularly skewed with respect to a corresponding Iris-Pupil plane 206 (not shown in FIG. 3) so that circular features on the Iris-Pupil plane appear elliptical on the sensor plane 302. In some embodiments, the sensors 102 may be image sensors such as, for example, complementary metal oxide semiconductor (CMOS) sensors and/or charge-coupled device (CCD) sensors. In such embodiments, the sensors 102 may generate eye tracking data in the form of pixel data that defines images of the eyes. These images may be formed based on ambient light surrounding the user. Thus, in contrast to conventional eye tracking systems that rely on illuminating the eye(s) with near infrared light to cause first Purkinje reflections (e.g., "glints") that are distributed around the iris, the techniques disclosed herein do not require active emission of near infrared light toward the user's eyes. The numerous benefits of the techniques disclosed herein include providing a system that can track the user's eyes using ambient light rather than having to expend battery resources to generate near infrared light. Moreover, the disclosed techniques provide a system that is highly sensitive and accurate in the detection of eye movements (e.g., the systems are sensitive enough to even accurately track saccadic eye movements).

Semi-axes for the "elliptically shaped" iris 108 and/or pupil 106 are uniquely oriented within the sensor plane 302 for any particular subtended angle of the sensor 102 and rotation of the eye being tracked. The size of the semi axes of the elliptically shaped iris 108 and pupil 106 depend on the original size of each and any magnification caused by optical components (e.g., lenses, etc.) of the sensor 102. In FIG. 3, the semi-major axis of the elliptically shaped iris 108 is labelled $p_{ip}^M$ and the semi-minor axis of the elliptically shaped iris 108 is labelled $p_{ip}^m$. The sensor plane 302 is illustrated with a sensor coordinate system centered thereon. The sensor coordinate system includes a vertical y-Axis and a horizontal x-Axis. Additionally, as illustrated, the elliptically shaped iris 108 is rotated an angle α with respect to the horizontal x-Axis. Therefore, within the sensor plane 302, an ellipse 204 that is centered at $(\bar{x}_{ip}^d, \bar{y}_{ip}^d)$ with semi-major axis $p_{ip}^M$ and semi-minor axis $p_{ip}^m$ and that is also rotated an angle α with respect to the horizontal x-Axis is given by Equation 1 shown below:

$$E_{ip}(i,j) = \{\bar{x}_{ip}^d + p_{ip}^M \cos[\varphi(i,j)]\cos(\alpha) - p_{ip}^m \sin[\varphi(i,j)]\sin(\alpha), \bar{y}_{ip}^d + p_{ip}^M \cos[\varphi(i,j)]\sin(\alpha) - p_{ip}^m \sin[\varphi(i,j)]\cos(\alpha)\} \quad (1)$$

Figure 4:
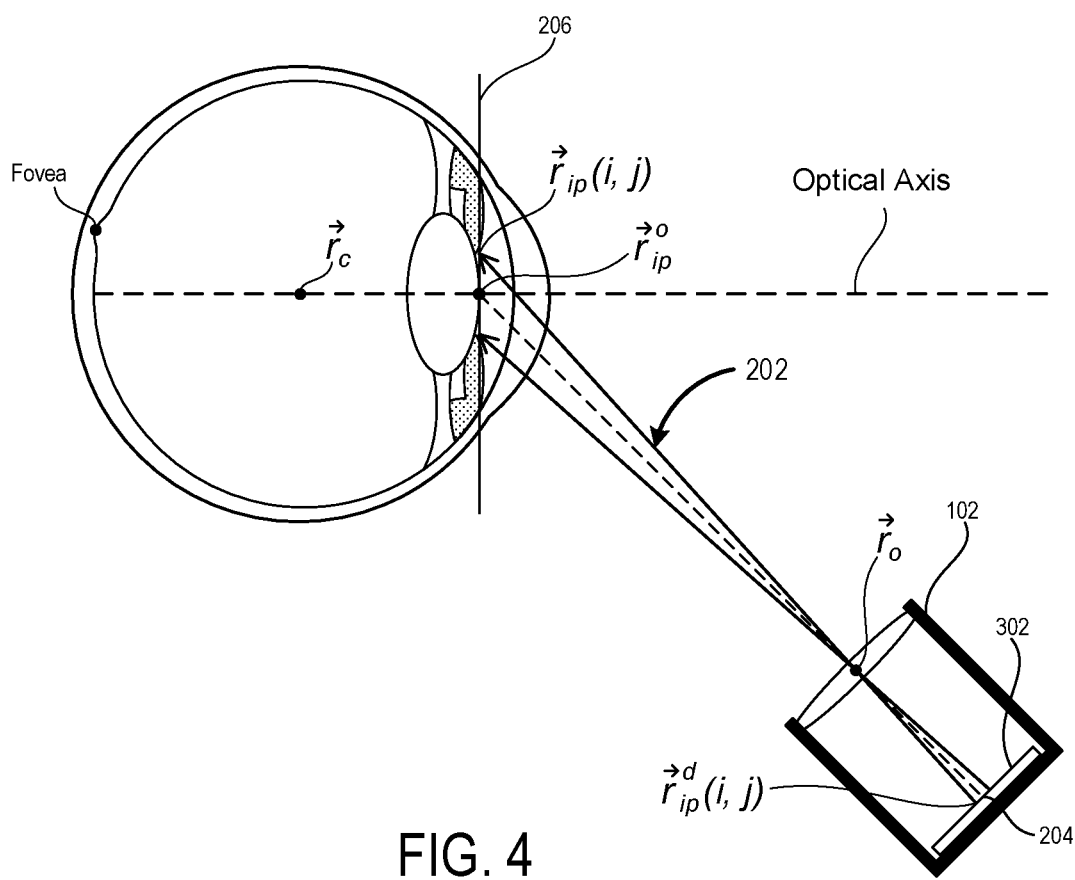
FIG. 4 illustrates a side view of a 3D propagation of the ellipse of FIG. 3 from the sensor plane through a predetermined point and toward the Iris-Pupil plane.

Turning now to FIG. 4, illustrated is a side view of a 3D propagation 202 of the ellipse 204 of FIG. 3 from the sensor plane 302 through a predetermined point. In the illustrated embodiment, the predetermined point is labeled $\vec{r}_o$ and is defined as the center of the entrance pupil for the sensor 102. To improve the clarity of the illustration, only two individual 3D rays of the 3D propagation 202 are shown. Each individual ray extends from a point on the sensor plane 302 that falls along the perimeter of the ellipse 204 through the point $\vec{r}_o$ and, ultimately, to a point on the Iris-Pupil plane 206 that falls along the perimeter of the pupil 106 or iris 108. In plain terms, the 3D propagation 202 represents the reverse of the projections of the pupil 106 or iris 108 through the point $\vec{r}_o$ and to the sensor plane 302. Thus, in three dimensional terms the rays that start from the sensor plane 302 and pass through point $\vec{r}_o$ (e.g., the center of the entrance pupil of the sensor 102) and then travel some additional distance to reach the circular perimeter of the pupil 106 or iris 108 at the Iris-Pupil plane 206 is given by Equation 2 shown below:

$$\vec{r}_{ip}^{\,d}(i,j) = \vec{r}_o + [\sqrt{p_{ip}^2 + d_{ipo}^2} + \sqrt{|D_{cip}(i,j)|^2 + f^2}]\hat{T}_{oip}(i,j) \quad (2)$$

where, $\vec{r}_o$ is a point at which all of the rays of a particular image cross prior to forming an image on the sensor plane 302, $d_{ipo}$ is the distance from the point $\vec{r}_o$ to the center of the iris/pupil $\vec{r}_{ip}^{\,o}$ (as labeled in FIG. 4), $D_{cip}$ is the radial distance between the center of the sensor 102 and the ellipse points $E_{ip}$, f is the focal length of the sensor 102, and $\hat{T}_{oip}$ (i,j) is the vector going from the points in the ellipse 204 to the point $\vec{r}_o$.

In some embodiments, the systems described herein may determine one or more of an orientation Rot ($\phi$, $\Theta$) of the Iris-Pupil plane 206, a radius $p_{ip}$ of the pupil 106 or iris 108 (e.g., whichever circular feature is being observed to perform eye tracking), and the distance $d_{ipo}$ from the point $\vec{r}_o$ to the center $\vec{r}_{ip}^{\,o}$ of the iris/pupil by analyzing the 3D propagations 202 with respect to an ocular rotation model. The ocular rotation model may be usable to model rotation of a circular feature of an eye around that eye's center of rotation $\vec{r}_c$. For example, an ocular rotation model may define coordinates of a circle with a center $\vec{r}_{ip}^{\,o}$ (i,j) and a radius $p_{ip}$ and that is rotated around the eye's center of rotation $\vec{r}_c$ an elevation angle $\Theta$ and azimuth angle $\phi$ as given by Equation 3 shown below:

$$\vec{r}_{ip}^{\,r} = Rot(\phi,\Theta) \cdot (\vec{r}_{ip}^{\,o} + \vec{r}_{ip}^{\,c}(i,j) - \vec{r}_c) + \vec{r}_c \quad (3)$$

where the position of the center of the circle is given by $\vec{r}_{ip}^{\,o} = \{\vec{x}_{ip}^{\,o}, \vec{y}_{ip}^{\,o}, \vec{z}_{ip}^{\,o}\}$, and the parametrized coordinates of the circle are defined as $\vec{r}_{ip}^{\,c}(i,j) = \{p_{ip}\cos\varphi, p_{ip}\sin\varphi, 0\}$. In various embodiments, the center of the iris/pupil circle and the center of rotation of the eye $\vec{r}_c$ are defined from one or more anatomical eye models such as, for example, the Gullstrand model, the Arizona model, the Liou-Brennan model, and/or the Navarro model. Moreover, as described in more detail below, a user-specific calibration may be performed to complete global minimization of the various parameters used in Equation 3 to customize the ocular rotation model to a specific user.

As a specific but non-limiting example, the orientation Rot ($\phi$, $\Theta$) of the Iris-Pupil plane 206, the radius $p_{ip}$ of the pupil 106 or iris 108, and the distance $d_{ipo}$ from the point $\vec{r}_o$ to the center $\vec{r}_{ip}^{\,o}$ of the iris/pupil are determined by minimizing the error between the 3D propagations 202 of the points detected (e.g., in the sensor plane 302) $\vec{r}_{ip}^{\,d}$ through the vector $\hat{T}_{cip}$ (i,j), and a circle of radius $p_{ip}$ rotated around the eye center $\vec{r}_c$. An exemplary such error minimization technique is given by Equation 4 shown below:

$$Err(p_{ip}, d_{ipo}, Rot(\phi, \Theta)) = \operatorname{argmin} \sum_{i,j} \left\| \vec{r}_{ip}^{\,d}(i,j) - \vec{r}_{ip}(i,j) \right\|^2 \quad (4)$$

It will be appreciated that upon determining the orientation Rot ($\phi$, $\Theta$) of the Iris-Pupil plane 206 and the distance $d_{ipo}$ from the point $\vec{r}_o$ to the center $\vec{r}_{ip}^{\,o}$ of the iris/pupil, the systems disclosed herein can then determine where an optical axis for a tracked eye begins and in which direction it propagates with respect to the sensor 102. Additionally, in embodiments that include two sensors 102 which are separated by a known distance, upon determining the location of the center $\vec{r}_{ip}^{\,o}$ of the pupil for both eyes in relation to the sensors 102, the systems disclosed herein can dynamically determine an interpupillary distance (IPD) for the user (as shown in FIG. 2).

Figure 5A:
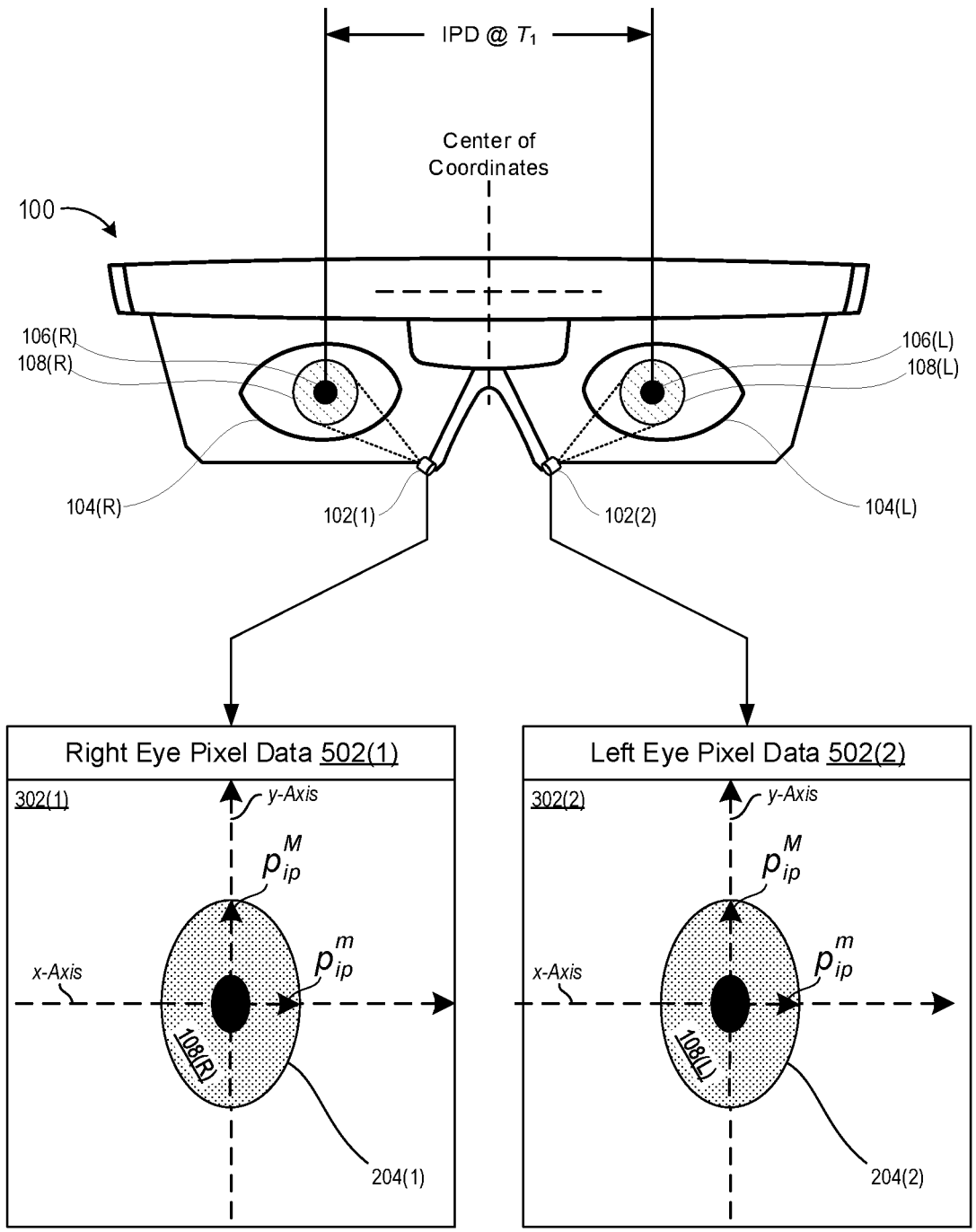
FIG. 5A illustrates exemplary eye tracking data in the form of pixel data that is generated by the sensors and that is usable to implement the techniques described herein.

Turning now to FIG. 5A, exemplary eye tracking data is shown in the form of pixel data 502 that is generated by the sensors 102 and that is usable to implement the techniques described herein. As illustrated in FIG. 5A, a NED device 100 includes a first sensor 102(1) that is angularly offset from and directed toward a user's right eye 104(R) and a second sensor 102(2) that is angularly offset from and directed toward a user's left eye 104(L). As the user's eyes move around to look at and/or track various objects within the user's field-of-view (FOV), the sensors 102 continually capture images of the pupils 106 and/or irises 108 of the user's eyes.

Similar to FIG. 1, FIG. 5A is illustrated from a particular perspective that is directly in front of the user's while the user's is looking straight forward. Thus, the optical axis of each of the eyes 104 is normal to the page and the pupils 106 and irises 108 are illustrated to be perfect circles. Since each of the sensors 102 is angularly offset from the optical axis of the particular eye that it is imaging, the pixel data 502 corresponding to each eye defines the pupils 106 and irises 108 as ellipses. As described above, these ellipses correspond to projections of the pupils 106 and irises 108 onto the corresponding sensor planes 302. Moreover, depending on the optical characteristics of the sensors 102 and/or lenses thereof, these projections may be defined by a series of rays that all pass through a common point such as the center of the entrance pupil of the sensor 102.

As described above, the ellipses that are formed by the projections of the pupils 106 and/or irises 108 onto the corresponding sensor plane 302 have unique orientations and semi-axes for any particular subtended angle of the sensor 102 and rotation of the eye being tracked. As illustrated in FIG. 5A, each of the right eye pixel data 502(1) and the left eye pixel data 502(2) define an image of a corresponding elliptically shaped iris 108. Each elliptically shaped iris 108 has a semi-major axis that is labelled $p_{ip}^M$ and a semi-minor axis that is labelled $p_{ip}^m$. The sensor planes 302 are each illustrated with a corresponding sensor coordinate system centered thereon. Each sensor coordinate system includes a vertical y-Axis and a horizontal x-Axis. Additionally, as illustrated, each elliptically shaped iris 108 is aligned with (e.g., centered on and not rotated with respect to) a corresponding sensor coordinate system. Thus, within each of the sensor planes 302(1) and 302(2), the perimeters of the right elliptically shaped iris 108(R) and the left elliptically shaped iris 108(L) define a first ellipse 204(1) and a second ellipse 204(2), respectively. Each of the ellipses 204 are centered at $(\bar{x}_{ip}^d, \bar{y}_{ip}^d)$ with semi-major axis $p_{ip}^M$ and semi-minor axis $p_{ip}^m$ and is not rotated respect to the horizontal x-Axis of their corresponding sensor plane 302.

Figure 5B:
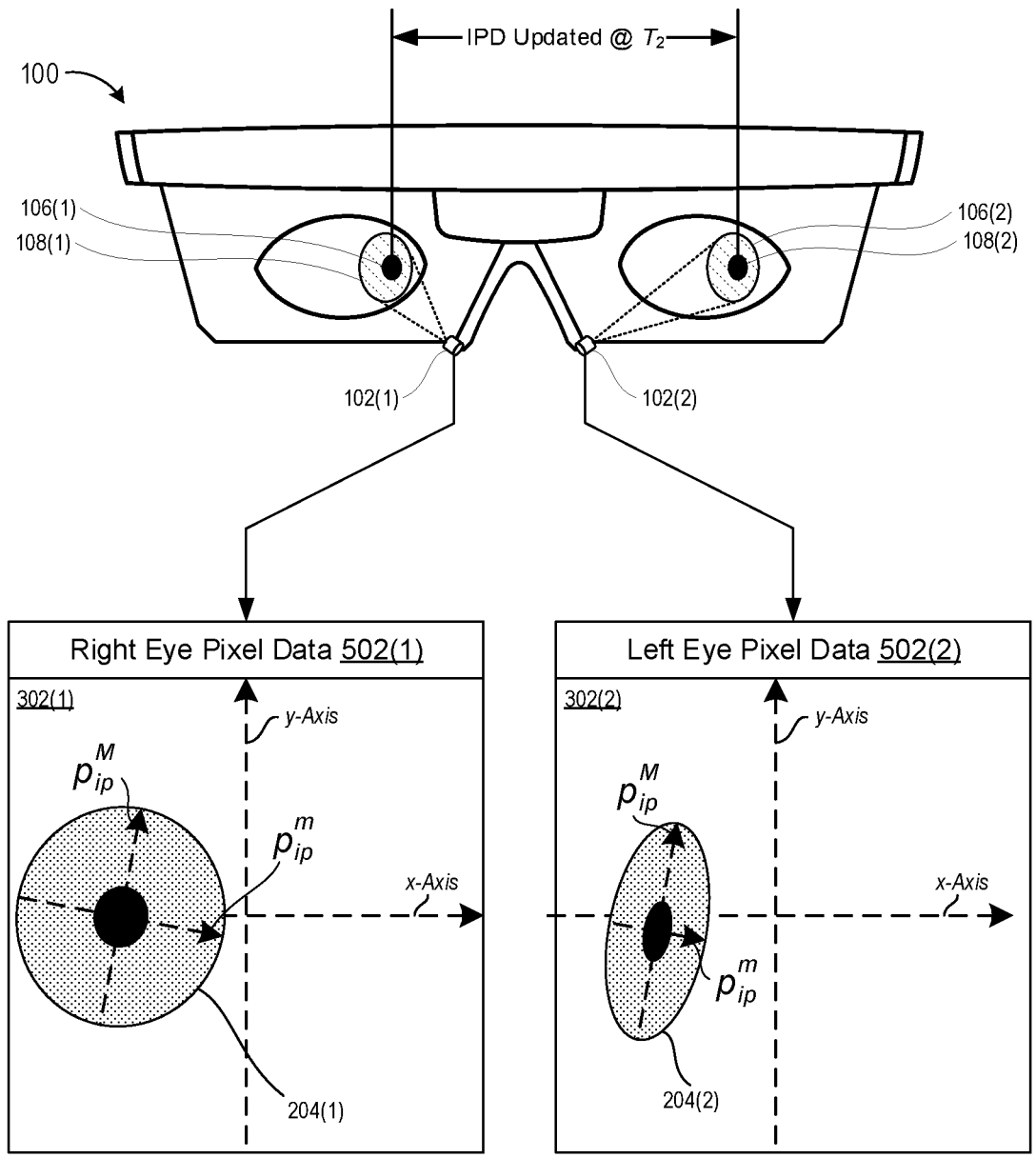
FIG. 5B illustrates exemplary eye tracking data in the form of pixel data that has changed in relation to FIG. 5A due to the user's focus shifting to the left.

Turning now to FIG. 5B, exemplary eye tracking data is shown in the form of pixel data 502 that has changed in relation to FIG. 5A due to the user's focus shifting to the left. As illustrated, the first ellipse 204(1) that corresponds to the projection of the user's right eye 104(R) has shifted and rotated in relation to the first sensor plane 302(1). Additionally, the semi-minor axis $p_{ip}^m$ of the first ellipse 204(1) has lengthened since the right eye's optical axis is directed more towards the sensor 102(1) in FIG. 5B (e.g., after the user looks left) that it was in FIG. 5A. As further illustrated, the second ellipse 204(2) that corresponds to the projection of the user's left eye 104(L) has shifted and rotated in relation to the second sensor plane 302(2). Additionally, the semi-minor axis $p_{ip}^m$ of the second ellipse 204(2) has shortened since the left eye's optical axis is directed more away from the second sensor 102(2) in FIG. 5B (e.g., after the user looks left) that it was in FIG. 5A.

In various embodiments, the eye tracking data for the user's two eyes may be used to continually and dynamically determine the current (e.g., real time) interpupillary distance (IPD) of the user. In particular, the eye tracking data may be analyzed to determine ellipse parameters that define the ellipses 204 for each eye within the corresponding sensor plane 302. Then, using the techniques described above with respect to equations 1 through 4, the center points $\vec{r}_{ip}^{\,o}$ for each eye may be determined with respect to the corresponding sensor 102. Since the sensors 102 are mechanically fixed at known locations and angles with respect to each other, the determined center points $\vec{r}_{ip}^{\,o}$ for the right eye 104(R) with respect to the first sensor 102(1) and the left eye 104(L) with respect to the second sensor 102(2) together yield the IPD at particular time at which the pixel data was captured. Thus, as shown in FIG. 5A, an IPD can be initially determined in association with pixel data that is captured at a first time $T_1$. Then, as shown in FIG. 5B after the user has looked to the left, an updated IPD can be determined can be determined in association with other pixel data that is captured at a second time $T_2$.

Figure 6:
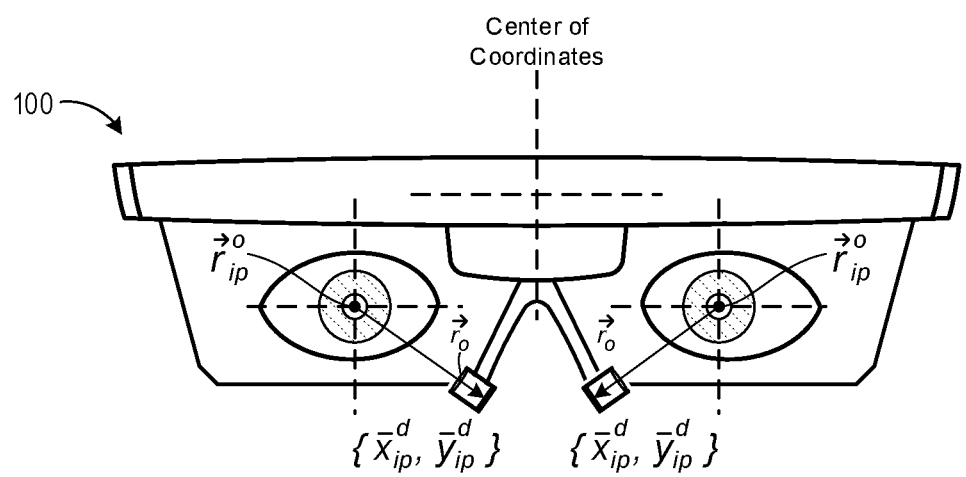
FIG. 6 illustrates exemplary positions of a user's fovea in relation to the optical axes of the user's left and right eyes.

Turning now to FIG. 6, illustrated is the exemplary NED device 100 with various geometrical features labeled thereon that are relevant to a specific technique for calculating the interpupillary distance (IPD). It can be appreciated that Equation 2 as described above can be modified to specifically place the center of the pupil $\vec{r}_{ip}^{\,d}$ (center) in space for both the left and right eyes. Specifically, Equation 2 can be modified into Equation 2.1 as shown below:

$$\vec{r}_{ip}^{\,d}(\text{center}) = \vec{r}_o + [d_{ipo} + \sqrt{D_{cip}(\text{center})^2 + f^2}] \hat{t}_{oip}(\text{center}) \qquad (2.1)$$

Then, once the center of the pupil for each of the right eye 104(R) and the left eye 104(L) have been placed in space, the IPD can be obtained as the norm of the subtraction of the projected pupillary axis for the left eye and the right eye—as given by Equation 5 below:

$$\text{Interpupilary Distance}(IPD) = \|\vec{r}_{ip}^{\,d}(\text{left,center}) - \vec{r}_{ip}^{\,d}(\text{right,center})\| \qquad (5)$$

Figure 7:
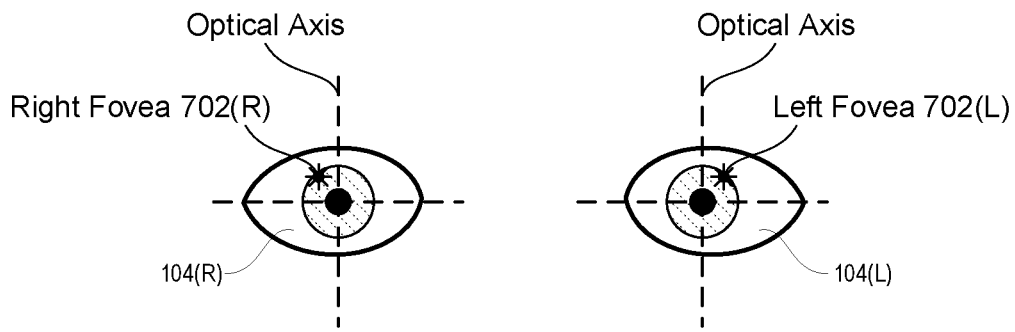
FIG. 7 illustrates exemplary positions of a user's right fovea and left fovea in relation to the optical axes of the user's right eye and left eye, respectively.

Turning now to FIG. 7, illustrated are exemplary positions of a user's right fovea 702(R) and left fovea 702(L) in relation to the optical axes of the user's right eye 104(R) and left eye 104(L), respectively. As can be seen from FIG. 7, the position of the fovea for each eye is eccentric (e.g., not centrally placed) regarding the optical axis of the corresponding eye. Generally speaking, the right fovea 702(R) tends to be positioned in the second quadrant for the right eye 104(R) whereas the left fovea 702(L) tends to be positioned in the first quadrant for the left eye 104(L). This is consistent with the illustrated positions of the fovea in FIG. 7. The fovea 702 is the specific region of the retina at which visual acuity is highest due to the user's retinal cones being particularly concentrated in this area. For this reason, the center of the user's field of vision for each eye is focused at the fovea for that eye. The result is that the user's visual axis passes through the center of the fovea 702 so that light from whatever object the user is currently focused on passes through the pupil and lens of the eye before ultimately striking the fovea 702.

Figure 8:
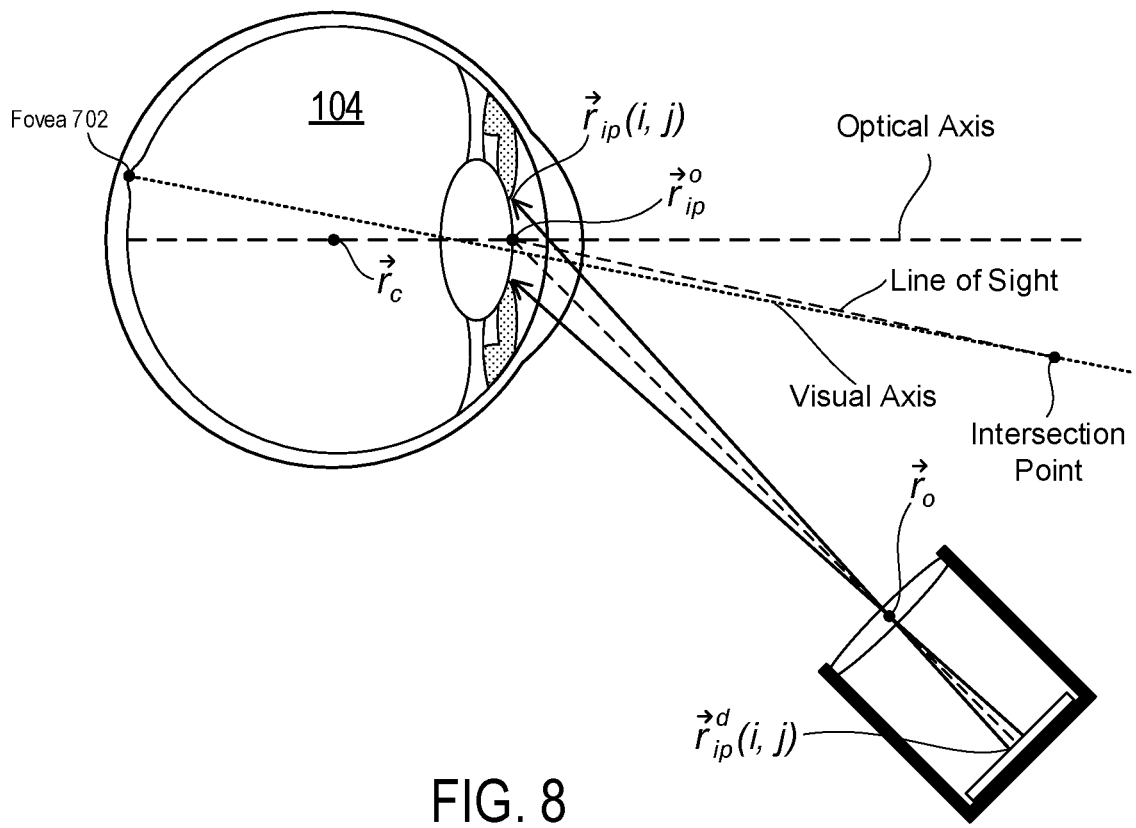
FIG. 8 illustrates a side view of a user's eye showing how the offset position of the user's fovea in relation to the optical axis results in the visual axis diverging from the optical axis.

Turning now to FIG. 8, illustrated is a side view of a user's eye 104 showing how the offset position of the user's fovea in relation to the optical axis results in the visual axis diverging from the optical axis. As illustrated, the fovea position being above the optical axis at the back of the user's eye results in the visual axis pointing down slightly. It should also be appreciated from the combination of FIGS. 7 and 8 that the visual axes of the user's eyes will also tent to be pointed inward slightly.

As shown in FIG. 8, a line of sight of the user extends from the center of the entrance pupil $\vec{r}_{ip}^{\,o}$ and intersects the visual axis at a singular intersection point. Accordingly, when the user is focused on an object at a particular accommodation plane, determining the user's line of sight may be adequate to determine where the user is focused. However, since the visual axis will be most closely directed at whatever object the user is focused on regardless of the depth at which the user is focused, conventional eye tracking methods that merely track the user's line of sight are inadequate for determining where the user is focused for all accommodation planes. By dynamically tracking the user's visual axis, the eye tracking systems disclosed herein are able to determine a vergence in space at which the user is currently focused independent of what accommodation plane that vergence falls on.

In some instances, convention eye tracking systems estimate the user's line of sight by observing the Purkinje reflections with the addition of head tracking information. Unfortunately, even an accurate estimation of the user's line of sight may be insufficient to accurately determine the depth at which the user is focusing within the real-world environment. This is because the user's line of sight and the user's visual axis (which actually propagates to the user's fovea) only converge at a single depth plane. Although the visual axis is illustrated as a straight and continuous line in FIG. 8, it will be appreciated by one skilled in the art that the actual optical path of the visual axis is more aptly described as a line connecting the fixation point (at which the user is focused) to the first and second nodal points (not shown in FIG. 8) and the user's Fovea.

Figure 9:
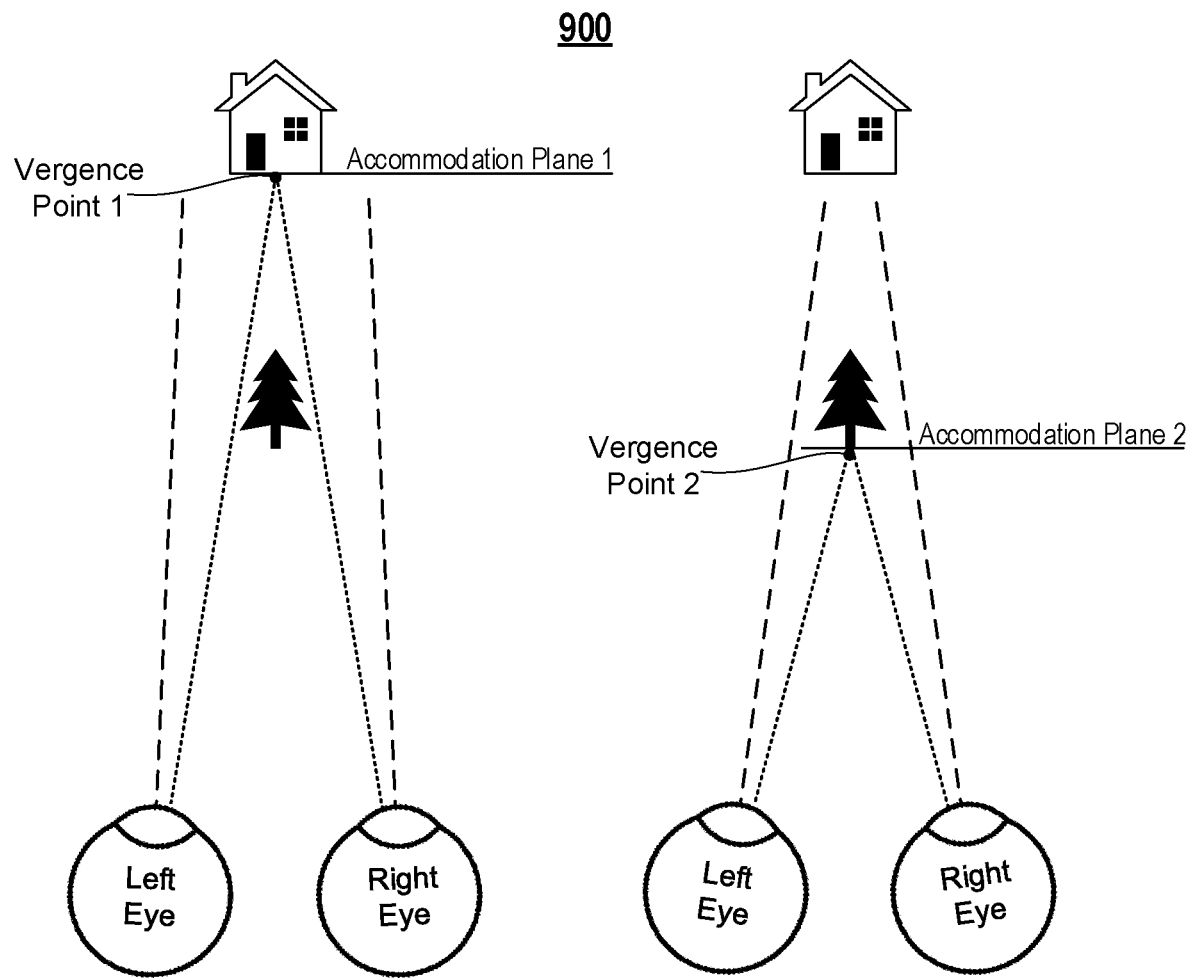
FIG. 9 illustrates an exemplary environment in which a user may perform vergence movements of the eyes to shift a vergence of the two visual axes (e.g., a focal point) from a first accommodation plane to a second accommodation plane.

Turning now to FIG. 9 to demonstrate the foregoing point, illustrated is an exemplary environment 900 in which a user may perform vergence movements of the eyes to shift a vergence of the two visual axes (e.g., a focal point) from a first accommodation plane to a second accommodation plane. It will be appreciated that vergence movements are closely connected to accommodation of the eye. Under normal conditions, changing the focus of the eyes to look at objects at different distances will automatically cause vergence and accommodation. This is sometimes referred to as the accommodation-convergence reflex. Generally speaking, a vergence movement comprises the simultaneous movement of a binocular system (e.g., the user's two eyes) in opposite directions to perform a depth operation. When the user performs a vergence movement to change a focus from a distant object to a relatively closer object, the eyes rotate toward each other (i.e., the eyes perform a convergence movement). When the user performs a vergence movement to change a focus from a close object to a relatively more distant object, the eyes rotate toward away from each other (i.e., the eyes perform a divergence movement).

The left side of FIG. 9 shows the focus of the user on a house at "Accommodation Plane 1" that is relatively farther from the user than "Accommodation Plane 2." Thus, on the right side of FIG. 9 the visual axes each reach a common vergence point that resides on the house whereas a vergence of the lines of sight (which conventional systems track) does not actually represent where the user is focused. The left side of FIG. 9 shows the focus of the user on a tree that is at an Accommodation Plane 2 that is relatively closer to the user. Thus, on the left side of FIG. 9 the visual axes each reach a common vergence point that resides on the tree whereas a vergence of the lines of sight again does not actually represent where the user is focused.

In some embodiments, visual axis offset data is used to continuously track the visual axis of the user's eyes 104. For example, it can be appreciated that by deploying various techniques as described above, the eye tracking systems described herein may continually determine the optical axis and the orientation Rot ($\phi$, $\Theta$) of the Iris-Pupil plane 206. Exemplary visual axis offset data defines a spatial relationship between the optical axis of the eye and/or the orientation Rot ($\phi$, $\Theta$) of the Iris-Pupil plane 206 of the eye 104. Thus, upon determining the optical axis and/or the orientation Rot ($\phi$, $\Theta$) for a particular eye, the eye tracking systems described herein may utilize the visual axis offset data to calculate the visual axis.

Figure 10:
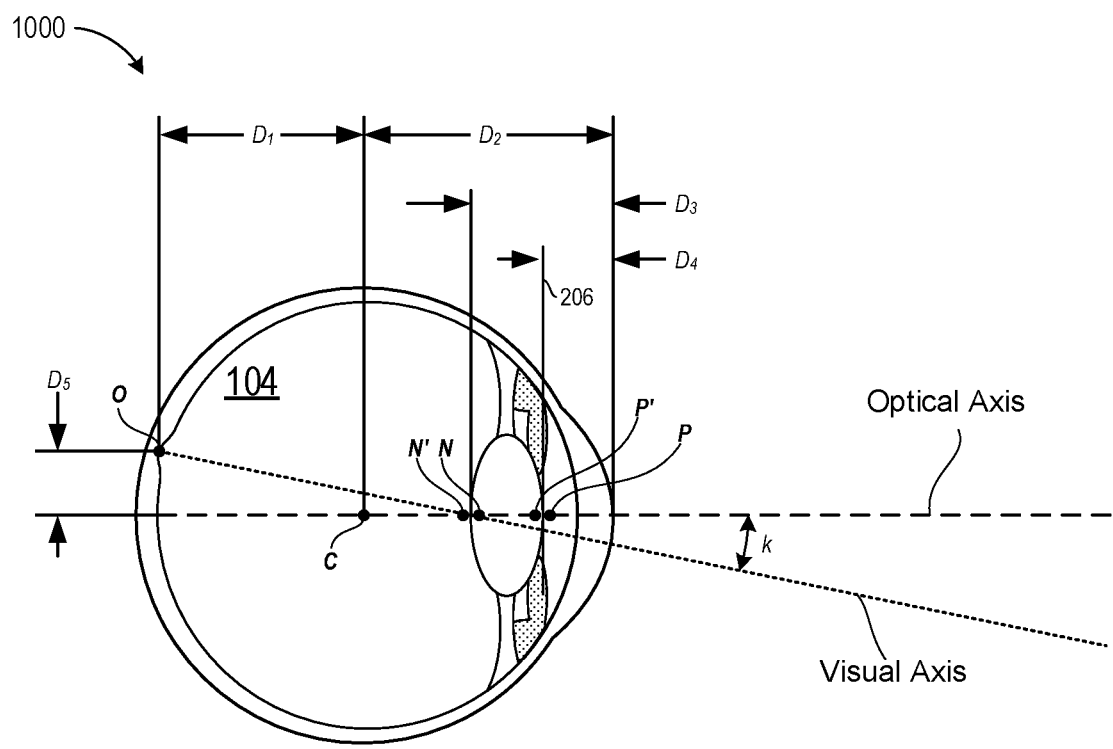
FIG. 10 illustrates an exemplary anatomical eye model that defines geometrical relationships between various portions of an eye.

Turning now to FIG. 10 to demonstrate the foregoing point, illustrated is an exemplary anatomical eye model 1000 that defines geometrical relationships between various portions of an eye 104. As illustrated, the anatomical eye model 1000 defines: a horizontal dimension $D_1$ from the center of the eye 104 (i.e., the point labeled "C") to the fovea (i.e., the point labeled "O"); a horizontal dimension $D_2$ from the center of the eye 104 (i.e., the point labeled "C") to the front surface of the cornea; a horizontal dimension $D_3$ from the front surface of the cornea to a rear surface of the lens of the eye 104 (i.e., the point labeled "N'"); a horizontal dimension $D_4$ from the front surface of the cornea to a front surface of the lens of the eye 104 (i.e., the point labeled "P'"); and a vertical dimension $D_5$ from the center of the eye 104 (i.e., the point labeled "C") to the fovea (i.e., the point labeled "O"). In various implementations, these or other dimensions may be used to define the visual axis offset data. The values for the relevant dimensions may be taken from any variety of suitable models that include, but are not limited to, the Gullstrand model, the Arizona model, the Liou-Brennan model, and/or the Navarro model.

As illustrated in FIG. 10, the visual angle $\vec{VA}_{N'}$ line may be represented as a vector that extends from the fovea at point "O" to the point labeled "N'" that represents the rear surface of the lens of the eye 104. The visual angle $\vec{VA}_{N'}$ line subtends an angle k from the optical axis and can be defined based on Equation 6 below:

$$\vec{VA}_{N'} = \frac{\vec{r}_{N'} - \vec{r}_O}{|\vec{r}_{N'} - \vec{r}_O|} = \frac{\vec{R}_{N'O}}{|\vec{R}_{N'O}|} \tag{6}$$

where $\vec{r}_{N'}$ is the image nodal position and $\vec{r}_O$ is the central position of the fovea 702. In general, literature has reported that the angle k ranges between 4 and 8 degrees.

It can be appreciated that by applying the definition of nodal points to the exemplary anatomical eye model 1000, there is a conservation of the angles regarding the optical axis. For this reason, the line that starts from the object nodal point "N" can be described by Equation 7 given below:

$$\vec{VA}_N = \vec{r}_N + D_{SN} \vec{VA}_{N'} \tag{7}$$

where $\vec{r}_N$ is the object nodal point and $D_{SN}$ is the distance between object nodal point "N" and the stimulus (e.g., object) upon which the user is focused.

Based on the foregoing, it can be appreciated that the rotation calculated from the minimization technique described in relation to Equation 4 as applied over $\vec{VA}_N$ regarding to the center $\vec{r}_c$ of the eye 104 must be equal to the vector joining the stimulus and the target as given by Equation 8 below:

$$\text{Rot}(\phi,\Theta)(\vec{R}_{SC} + \|\vec{R}_{SC}\| \vec{VA}_{N'}) = \vec{R}_{SC} \tag{8}$$

It can be appreciated that the various nodal points that are illustrated in FIG. 10 and described throughout this document will change in relative position as the user focuses on object at different accommodation planes. For example, in focusing on objects at different depths, the lenses of the eyes are of course caused to change shape. As these shape changes occur the rear surface of the lens may shift between the nodal point labeled "N" and the nodal point labeled "N'" whereas the front surface of the lens may shift between the nodal point labeled "P" and the nodal point labeled "P'." Notable, these changes in the shape of the lens and positions of the nodal points that are triggered by accommodation changes have an insignificant impact on the orientation and placement of the visual axis within the eye. For this reason, in various embodiments the visual axis offset data may define relationships between the optical axis of the eye in a manner that is independent of the current accommodation plane upon which the user is focused.

Figure 11:
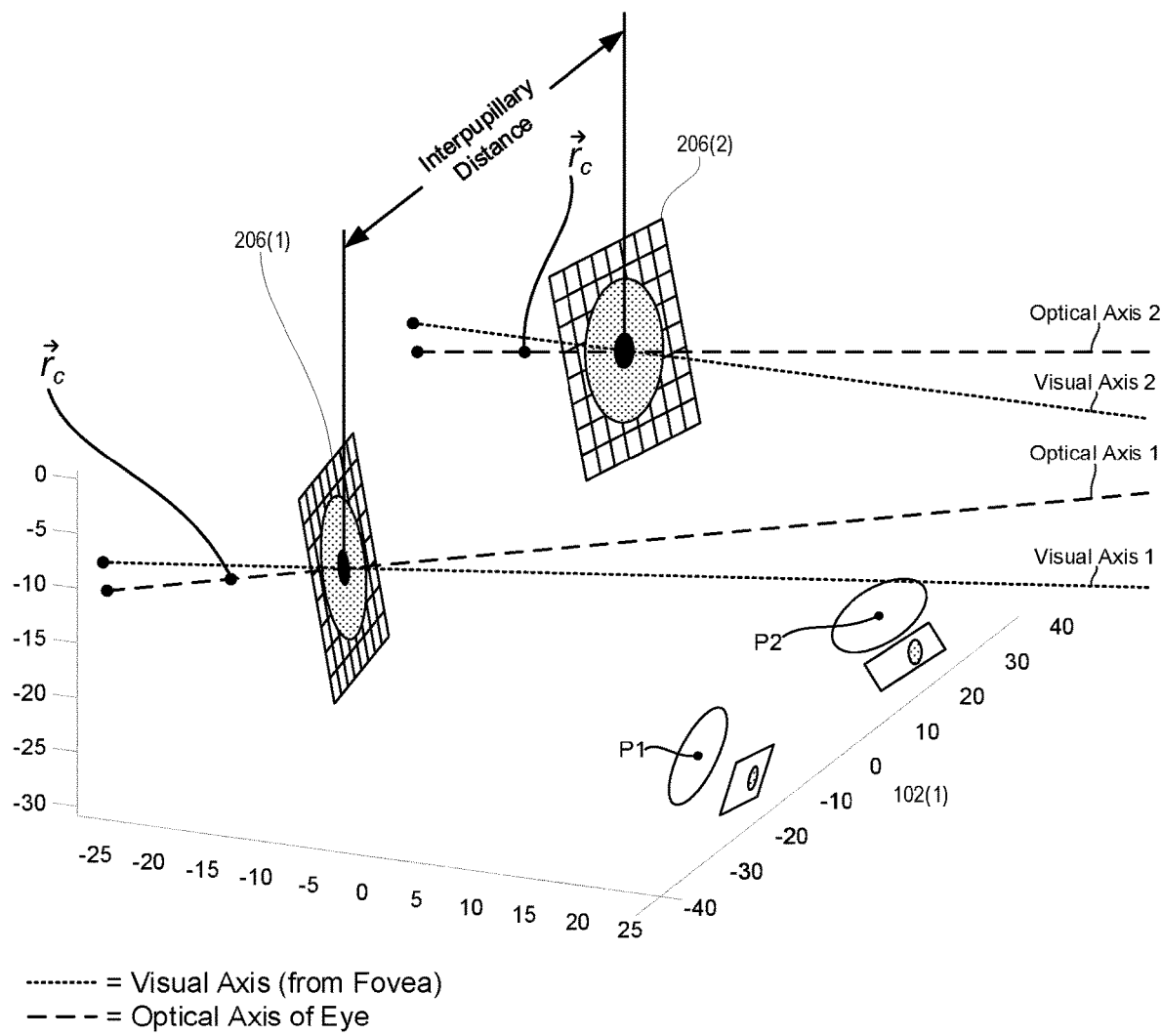
FIG. 11 illustrates a pair of visual axes that are determinable based on visual axis offset data defining a spatial relationship between the individual visual axes and corresponding optical axes.

To illustrate the foregoing, FIG. 11 illustrates a pair of visual axes that are determinable based on visual axis offset data defining a spatial relationship between the individual visual axes and corresponding optical axes. As illustrated in FIG. 10, upon determining the optical axis and the orientation Rot ($\phi$,$\Theta$) of the Iris-Pupil plane 206 for each eye 104, the eye tracking systems described herein can then calculate the visual axes for each eye. These calculations may be done continuously based on visual axis offset data that defines a spatial relationship between the optical axis of the eye and/or the orientation Rot ($\phi$, $\Theta$) of the Iris-Pupil plane 206 of the eye 104.

In some embodiments, upon calculating the pair of visual axes for a particular moment in time, the eye tracking system may then determine the vergence of the visual axes in space. The two visual axes will rarely actually converge in space perfectly. This is because although generally modeled as such, the human body does not behave perfectly symmetrically. Rather, there are slight variations in where the two eyes will actually be pointed in a real-life scenario. As such, in various embodiments, the vergence is calculated by performing minimization techniques with respect to both of the two visual axes. Stated plainly, based on the assumption that the two visual axes will be closest to actually converging at or very near the point in space that the user is actually focusing, the techniques described herein may determine the vergence point to be the point in space at which the visual axes are closest together.

Figure 12:
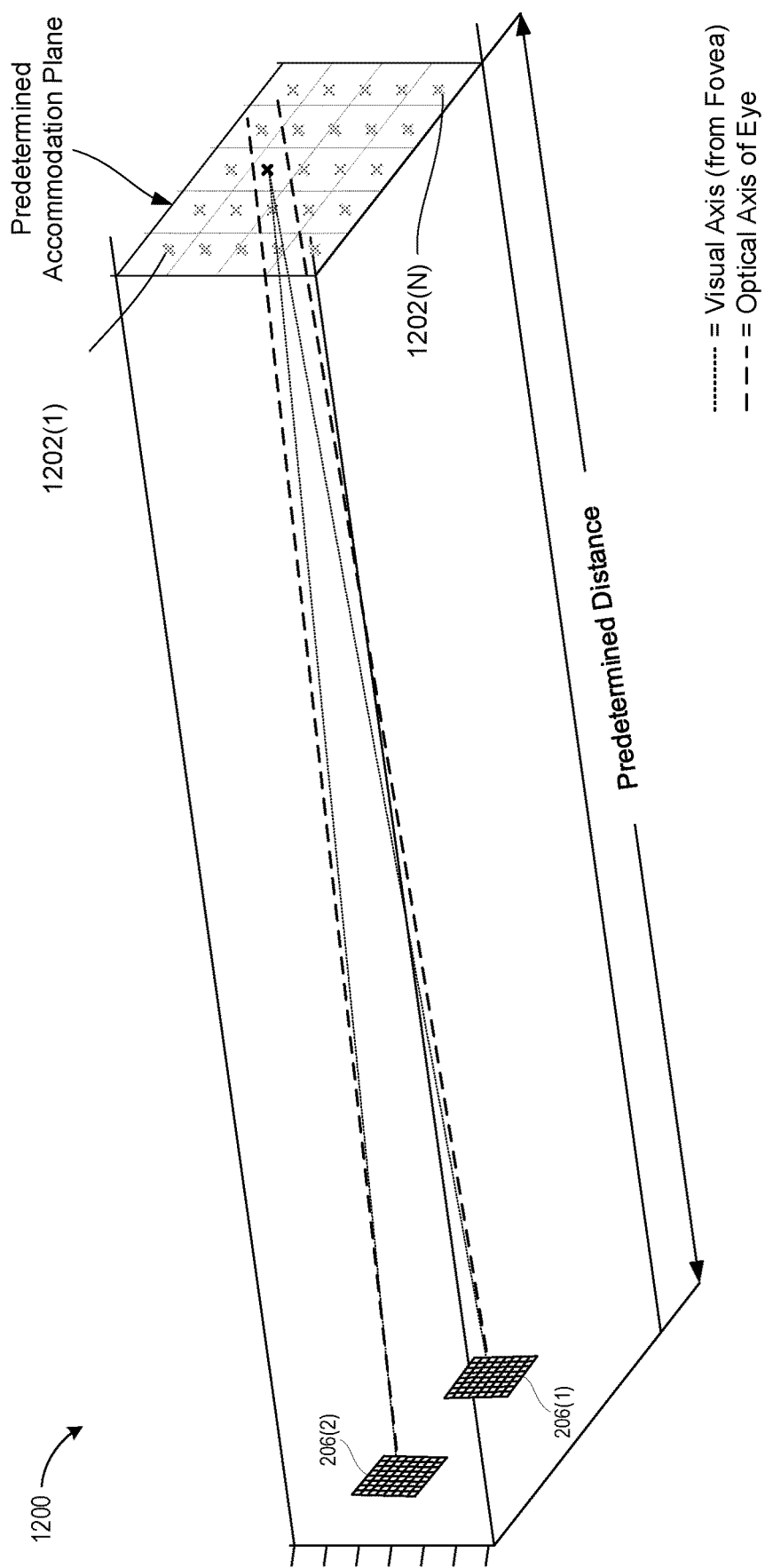
FIG. 12 illustrates an exemplary environment in which a plurality of virtual stimuli can be sequentially generated at a predetermined accommodation plane for performance of a user-specific calibration process.

Turning now to FIG. 12, illustrated is an exemplary environment 1200 in which a plurality of virtual stimuli 1202 can be sequentially generated at a predetermined accommodation plane for performance of a user-specific calibration process. As illustrated, the plurality of virtual stimuli 1202 may be uniformly spaced in a predetermined grid shaped pattern at a predetermined accommodation plane. The predetermined accommodation plane may be spaced a predetermined distance in front of the NED device 100 (not shown in FIG. 12). As a specific but non-limiting example, the predetermined accommodation plane may be spaced a distance of two meters in front of the user. It should be appreciated that as the stimuli are virtual in nature, the virtual stimuli may be generated at the accommodation plane of two meters by a display element (e.g. a waveguide display) that is located at a much closer distance to the user's eyes than two meters. For example, modern NED devices are capable of rendering images at a plurality of accommodation depths all from a transparent display that is positioned between fifteen and thirty-five millimeters from the user's eyes.

To perform the user-specific calibration process, individual ones of the virtual stimuli 1202 are sequentially rendered (e.g., one at a time) to cause the eyes of the subject to rotate so that the visual axes converge at the currently rendered virtual stimuli. Then, the discrepancy between the orientations Rot (ϕ, Θ) of the Iris-Pupil plane 206 as the user's focus changes between the individual stimuli can be exploited to determine the optimum visual axis for that specific user. Stated plainly, the visual axis offset data can be customized for the specific user.

During performance of the user-specific calibration process, the orientation Rot (ϕ, Θ) of the Iris-Pupil plane 206 while the user is focused on each individual one of the virtual stimuli 1202. Then, various error minimization techniques can be deployed to determine what the optimum visual axis is for the user. As a specific example of such an error minimization technique is given by Equation 9 as shown below:

$$Err(\vec{VA}_{N'}) = \sum_{i=1}^{m}\sum_{j=1}^{n} \left\| Rot(\phi, \Theta, i, j)(\vec{R}_{SC}(i,j) + \|R_{SN}\|\vec{VA}_{N'}) - \vec{R}_{SC}(i,j) \right\|^2 \quad (9)$$

This type of minimization technique has the advantage that it is convex and that the visual axis can be calculated analytically. Furthermore, while the coordinates of the stimulus are known $\vec{r}_S$, the values of the center of rotation of the eye $\vec{r}_C$, and the object nodal point $\vec{r}_N$ can be either introduced following anatomical models like Gullstrand, Arizona, Liou-Brennan or Navarro among others, or otherwise, a global minimization can be performed for custom values.

Figure 13:
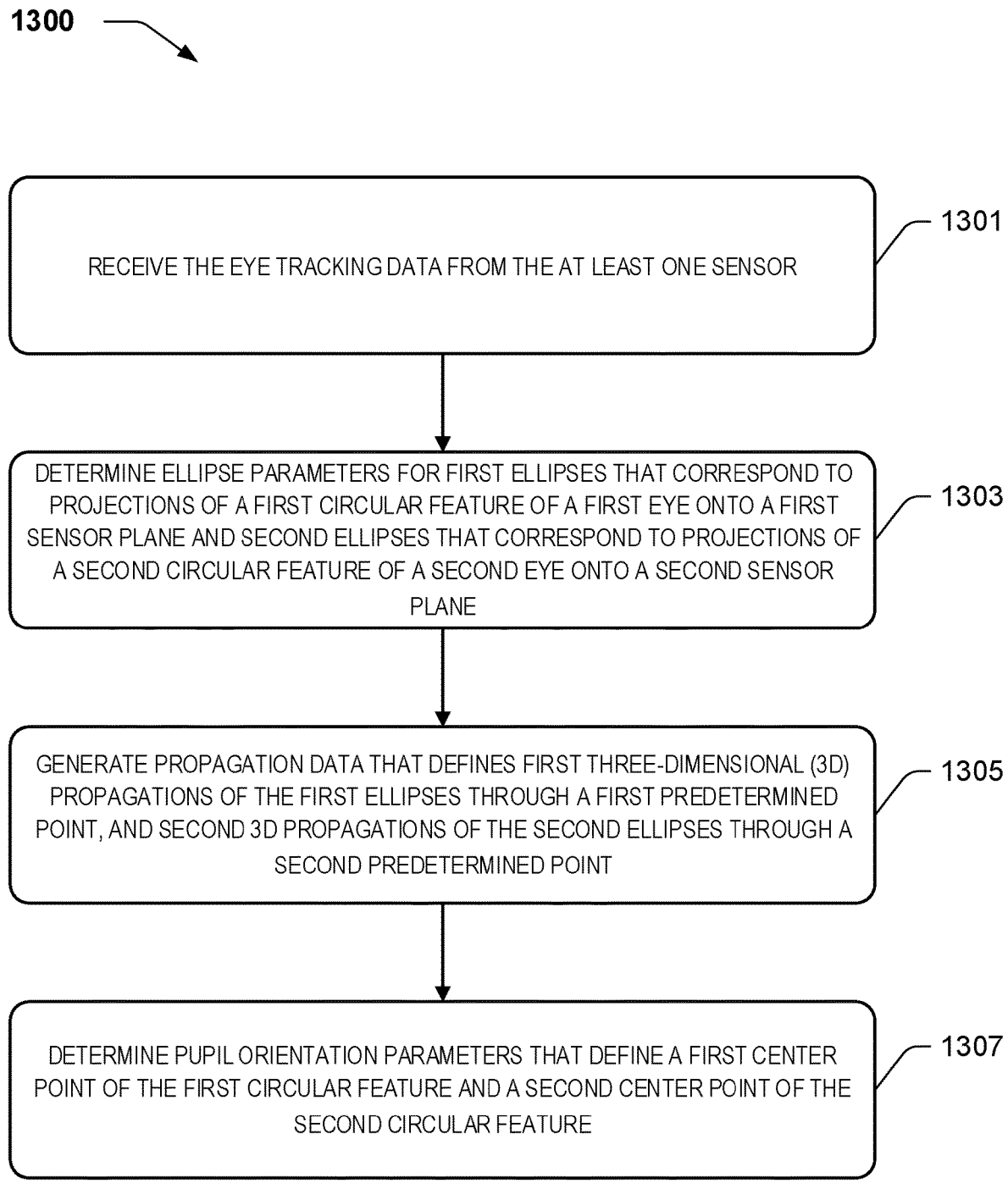
FIG. 13 is a flow diagram of a process 1300 to generate propagation data that defines three-dimensional (3D) propagations from ellipses detected at a sensor plane to determine pupil orientation parameters.

Turning now to FIG. 13, a flow diagram is illustrated of a process 1300 to generate propagation data that defines three-dimensional (3D) propagations from ellipses detected at a sensor plane to determine pupil orientation parameters. The process 1300 is illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform or implement particular functions. The order in which operations are described is not intended to be construed as a limitation, and any number of the described blocks can be combined in any order and/or in parallel to implement the process. Other processes described throughout this disclosure shall be interpreted accordingly.

At block 1301, an eye tracking system receives eye tracking data from at least one sensor that is directed toward at least one eye. As described herein, the at least one sensor can be a camera that includes at least one lens through which light passes prior to striking an image sensor (e.g., a CMOS sensor or any other suitable type of image sensor). The eye tracking data may be in the form of pixel data that defines an image of circular feature(s) of the at least one eye. In an exemplary embodiment, the eye tracking data includes images of both a right eye and a left eye of a user of a NED device. Moreover, as described above, the images may include elliptical representations of the circular features of the eyes due to a sensor plane in each of the sensors being angularly offset from an Iris-Pupil plane of the respective eye that each sensor is tracking. In various implementations, the eye tracking system may select between tracking the pupil vs the iris depending on physical characteristics of the user. For example, if the user has very dark irises, there may be very little contrast between the user's pupils and the user's irises. The result of this lack of contrast may be that tracking the user's pupil is impractical. In such a case, the eye tracking system may use the user's iris to perform the eye tracking since there will be greater contrast between the user's iris and the sclera (commonly referred to as the "white of the eye") of the user's eyes than between the user's "dark" iris and the user's dark pupil.

At block 1303, the eye tracking system may determine ellipse parameters for first ellipses that correspond to projections of a circular feature of a first eye (e.g., a right eye) onto a first sensor plane and also for second ellipses that correspond to projections of a circular feature of a second eye (e.g., a left eye) onto a second sensor plane. For example, the system may determine, for each of the first ellipse and the second ellipse, a center-point for the ellipse, a semi-major axis of the ellipse, a semi-minor axis of the ellipse, and an angular rotation of the ellipse with respect to a sensor plane.

At block 1305, the eye tracking system may generate propagation data that defines first 3D propagations of the first ellipse back toward the first eye and second 3D propagations of the second ellipse back toward the second eye. In various embodiments, each of the 3D propagations may comprise a series of lines that all begin at a point along the perimeter of an ellipse that is detected on a sensor plane and then propagation through a predetermined point back toward the eye of a user. It should be appreciated that the 3D propagations described herein may be generally understood as mathematical representations of rays of light rather than actual projections of light that are emitted from the eye tracking system toward the user. Notable, a major benefit of the eye tracking systems and techniques disclosed herein is that light need not be emitted for implementations—rather the eye tracking data can be generated based exclusively on ambient light.

At block 1307, the eye tracking system may utilize the propagation data to determine pupil orientation parameters that define various characteristics of the user's eye(s). Exemplary pupil orientation parameters may define optical axes for one or both of the user's eyes (e.g., an axis of an eye lens), visual axes for one or both of the user's eyes (e.g. axes that extend from the fovea through the lens and into the real-world environment), rotational angles of the user's eyes (e.g. an angle of rotation between a semi-axis of an ellipse and a horizontal axes of the sensor), Iris-Pupil Planes of the user's eyes (e.g. a plane on which the pupil resides), center points for the user's eyes (e.g., a point at which the optical axis (or alternatively the visual axis) intersects the Iris-Pupil plane). Additionally, or alternatively, the pupil orientation parameters may define various other characteristics of the user's eyes.

As described above, in various embodiments the eye tracking system may utilize the pupil orientation parameters and visual axis offset data to determine visual axes that correspond to each of the eyes of the user. Then, the eye tracking system may perform various minimization techniques to determine a vergence between the two visual axes. The determined vergence then represents a focal point within the real-world environment at which the user is currently focused. The vergence may be determined by calculating the point in space at which the two visual axes come the closest to actually converging in pure mathematical terms since in a practical sense the calculated visual axes for a user will rarely (if ever) actually converge.

The foregoing description provides a novel mathematical framework for enabling a variety of eye tracking techniques. As described in detail above, principle benefits of the novel mathematical framework include that the techniques it enables needn't rely on dedicated light sources to illuminate the eyes (e.g., to form Purkinje reflections from near infrared light) as many conventional eye tracking systems do to observe the eye orientation. Rather, under even dimly lighted environmental circumstances, the eye tracking techniques described herein may deploy cameras to observe a user's eyes under ambient light alone. Then, based on eye tracking data generated by the cameras and a presumption of the pupils and/or irises being substantially circular features, the techniques described herein determine ellipse parameters associated with an angular offset of the sensor planes (e.g., of the cameras) with respect to the Iris-Pupil Planes. Ultimately, the ellipse parameters may be utilized to determine various characteristics of the user's eyes such as, for example, directions of optical axes (e.g., an axis of an eye lens), directions of visual axes (e.g. axes that extend from the fovea through the lens and into the real-world environment), rotational angles (e.g. an angle of rotation between a semi-axis of an ellipse and a horizontal axes of the sensor), Iris-Pupil Planes (e.g. a plane on which the pupil resides), and/or center points for the user's eyes (e.g., a point at which the optical axis (or alternatively the visual axis) intersects the Iris-Pupil plane).

It will be appreciated by one skilled in the art that complete solutions the novel mathematical framework described above may be accomplished in a variety of forms. Various individual ones of these forms may rely upon a variety of assumptions. As described below, assumptions may be selected in order to simply and/or enable calculations of a complete solution to the mathematical framework described above. As a specific example, an assumption as to the size (e.g., diameter or radius) of an iris may be made to simply a complete solution to obtaining eye tracking information—thereby reducing the computational resources required to perform eye tracking techniques. As further described below, in various implementations certain assumptions may be made or not to achieve a desired level of accuracy of the resulting eye tracking information. For example, in some instances certain assumptions may simply the calculations to a complete solution of the mathematical framework at the expense of some level of accuracy. Various individual ones of the various forms of a complete solution may utilize a variety of equations including, but not limited to, those equations provided and described below.

Figure 14:
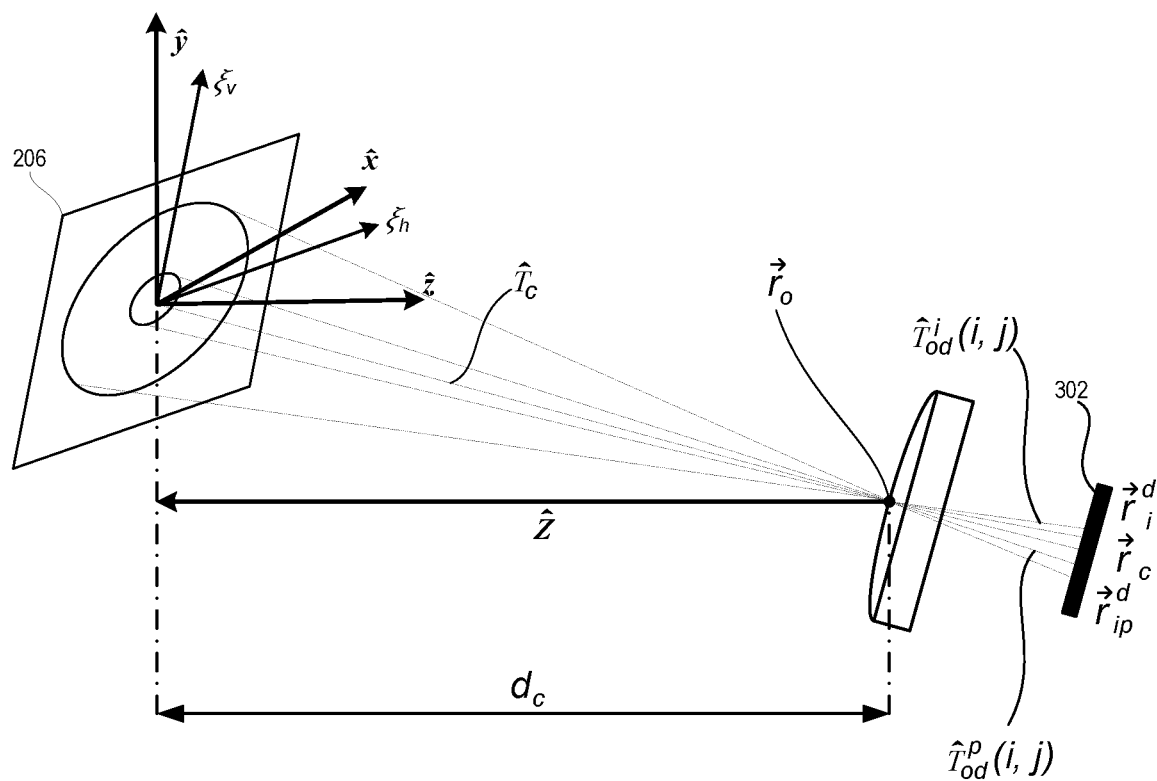
FIG. 14 illustrates an exemplary schematic diagram of a model geometry that corresponds to an analytical solution to a mathematical framework.

Turning now to FIG. 14, illustrated is an exemplary schematic diagram of a model three-dimensional (3D) geometry that corresponds to an analytical solution to the novel mathematical framework described above. Generally speaking, the analytical solution described in detail below provides techniques for calculating a location and an orientation of the Iris-Pupil Plane in spatial relation to a known position of a camera (e.g., a pinhole-type camera without optical distortion effects, a camera having one or more lenses). Furthermore, the analytical solution described in detail below utilizes an assumption of a predetermined presumed iris diameter to effectively reduce the computational complexity of solving the novel mathematical framework described above. It will be appreciated that by setting an assumption as to the iris diameter, the system of equations outlined below can be solved to yield the orientation of the Iris-Pupil Plane with respect to the camera and the distance of the Iris-Pupil Plane from the cameras—thus completing a mathematical reconstruction of the entire three-dimensional (3D) geometry shown in FIG. 14. In this way, the analytical solution reduces the number of processing cycles performed to yield a complete solution to the novel mathematical framework—thereby increasing the computational efficiency of the techniques described herein.

In some embodiments, the predetermined presumed iris diameter is set to an average diameter for a populace of subject users. For example, under circumstances where a populace of subject users have iris diameters ranging from 10.3 mm to 13 mm with an average diameter being 11.8 mm, then presuming the diameter of the iris to be 11.8 mm simplifies the nature of solving the system of equations outlined below. It has been found that presuming an iris diameter yields reasonable eye tracking accuracy for most applications. This is because the iris size is largely consistent across large groups of users with a large number of subjects having iris sizes tightly grouped around the average for the group. Exploiting this consistency by assuming a predetermined presumed iris diameter enables a fast and highly accurate estimation of where the Iris-Pupil Plane resides in space with respect to the cameras—in terms of both distance and orientation. Since the locational properties of the cameras are known (i.e., the location and orientation of the cameras with respect to one another are known for the NED device 100), one or both of the user's optical axis and/or visual axis can be calculated using the techniques described below. It can further be appreciated that the iris and pupil are nearly concentric in real life since the iris actually forms the pupil. Thus, the equations and techniques outlined herein may presume (where beneficial for enabling and/or simplifying calculations) that the iris and pupil of a particular eye are perfectly concentric.

With particular reference to FIG. 14, it will be appreciated that a circle that is embedded in a plane (e.g., an Iris-Pupil Plane 206) rotating about a center-point can be described trigonometrically as shown in FIG. 14, where and $\xi_v$ and $\xi_h$ are the angles of the plane with respect to a reference plane. In an exemplary implementation, the reference plane may be defined by a mechanical frame at which a camera is mounted to observe an eye of the user. In order to produce a 3D reconstruction of the model 3D geometry shown in FIG. 14, the pixels representing the pupil contour (e.g., as shown in FIGS. 5A and 5B) may be isolated from the rest of the eye. Then, these isolated pixels may be fitted to an ellipse. As a specific but non-limiting example, the isolated pupil contour may then be fitted to an ellipse (which may of course be tilted within the sensor plane) using a least square algorithm. It should be appreciated that a tilted ellipse that is provided by Equation 4 from above produces the outputs of: the eccentricity of the ellipse which is a ratio between the semi-major axis and semi-minor axis as represented by $$e^2 = 1 - \frac{p_m^2}{p_M^2};$$

the tilting angle $\alpha$; and the position of the center of the resulting ellipse $(\bar{x}_{ip}^d, \bar{y}_{ip}^d)$. Those pixels that are fitted to the tilted ellipse provide a two-dimensional (2D) distance with respect to the position (e.g., as denoted by $\vec{r}_o$) and orientation of the camera.

Figure 15:
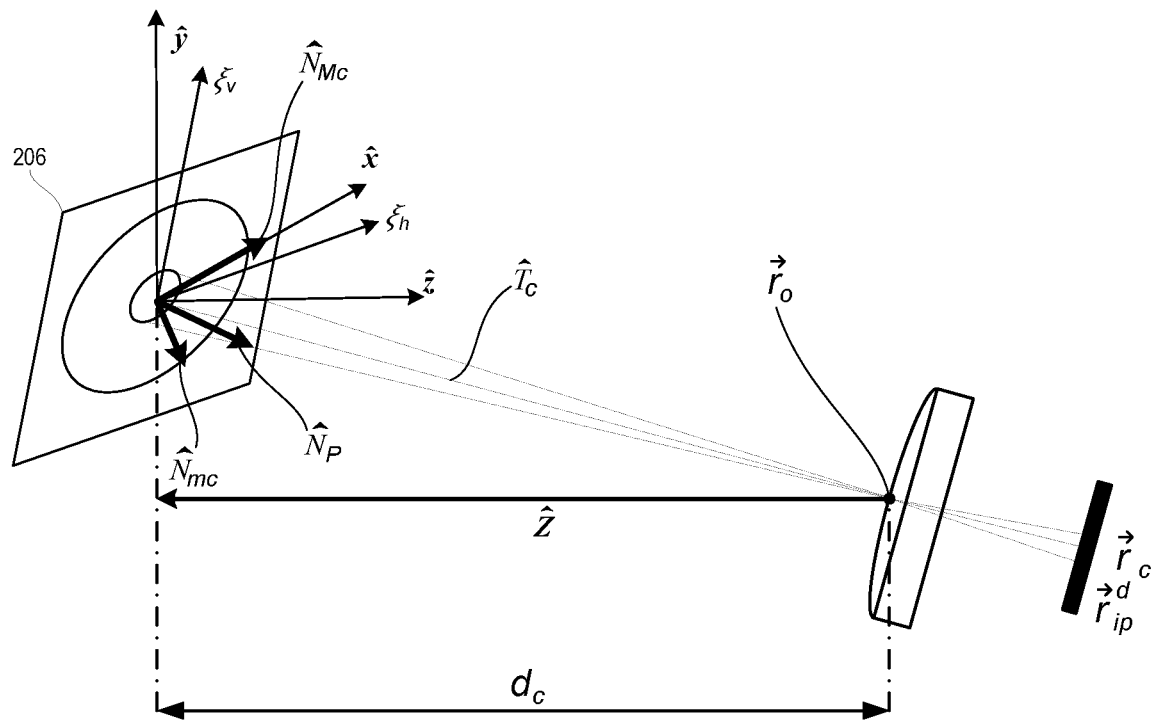
FIG. 15 illustrates an exemplary schematic that shows a representation of the Iris-Pupil Plane characteristic vector $\hat{N}_p$ within the model 3D geometry that corresponds to the analytical solution to the mathematical framework.

Turning now to FIG. 15, illustrated is an exemplary schematic that shows a representation of the Iris-Pupil Plane characteristic vector $\hat{N}_p$ within the model 3D geometry that corresponds to the analytical solution to the novel mathematical framework described above. FIG. 15 differs from FIG. 14 in that 3 orthonormal vectors (e.g., orthogonal and normalized vectors) that form a base are illustrated. It will be appreciated that by defining these 3 orthonormal vectors as $\{\hat{U}, \hat{V}, \hat{N}\}$, wherein $\hat{N}$ is defined as being normal to the sensor plane, and $\hat{U}$ and $\hat{V}$ are defined as being normal vectors of each other and of $\hat{N}$, then any point in the sensor can be expressed in the plane coordinates as Equation 10:

$$\vec{r}_{ip}^d(i,j) = \vec{r}_o + f\hat{N} + x_{ip}^d(i,j)\hat{U} + y_{ip}^d(i,j)\hat{V} \quad (10)$$

where $\vec{r}_{ip}^d(i,j)$ is the position of the point (e.g., a pixel) on the sensor plane, and where the columns of the pixels are given by $(y_{ip}^d = \bar{x}_{ip}^d + p_{ip}^M \bar{y}_{ip}^d + p_{ip}^M \cos[\varphi(i,j)]\sin(\alpha) + p_{ip}^m \sin[\varphi(i,j)]\cos(\alpha)$ while the rows of the pixels are given by $(x_{ip}^d = \bar{x}_{ip}^d + p_{ip}^M \cos[\varphi(i,j)]\cos(\alpha) - p_{ip}^m \sin[\varphi(i,j)]\sin(\alpha)$.

Turning back now to FIG. 14, vectors $\hat{T}_{od}(i,j)$ are shown that join individual pixels on the sensor plane 302 with the exit pupil $\vec{r}_o$ to provide individual geometrical propagations to individual points on the projected ellipse $\vec{r}_{ip}^d(i,j)$. More specifically, a vector $\hat{T}_{od}^i(i,j)$ is shown that joins individual pixels of the iris on the sensor plane 302 with the exit pupil $\vec{r}_o$ to provide individual geometrical propagations to individual points on the projected iris ellipse and another vector $\hat{T}_{od}^p(i,j)$ is shown that joins individual pixels of the pupil on the sensor plane 302 with the exit pupil $\vec{r}_o$ to provide individual geometrical propagations to individual points on the projected pupil ellipse. As indicated above, in various embodiments the exit pupil $\vec{r}_o$ may be defined as the center of a lens. Alternatively, the exit pupil $\vec{r}_o$ may be defined as the center of an aperture (e.g., a "pinhole" in lens-less implementations). The vector(s) $\hat{T}_{od}(i,j)$ that are shown in FIG. 14 may be mathematically represented by equation 11 below:

$$\hat{T}_{od}(i,j) = \frac{\vec{r}_o - \vec{r}_{ip}^d(i,j)}{\|\vec{r}_o - \vec{r}_{ip}^d(i,j)\|} \quad (11)$$

Recalling now the valid presumption that each of the iris and pupil are circular (as they each almost perfectly are in real life), it will be appreciated that this circular feature may be mathematically inscribed onto the Iris-Pupil Plane. As a specific example, a radius of the iris $p_i$ or pupil $p_p$ that is projected in between the center of the ellipse and the individual points on the ellipse may be described by equation 12 below:

$$\left\| \left( \frac{d_c + p_{ip}\tan\xi_h\cos\alpha + p_{ip}\tan\xi_v\sin\alpha}{\hat{T}_{od}(i,j)\cdot\hat{z}} \right) \hat{T}_{od}(i,j) - \frac{d_c}{\hat{T}_c\cdot\hat{z}} \right\| = p_{ip} \quad (12)$$

where $d_c$ is the projected distance onto the $\hat{z}$ axis of the translation $\hat{T}_c$ of the center of the ellipse, and where $p_{ip}$ is either the radius of the iris $p_i$ or the pupil $p_p$, and where $\tan \xi_h$ is the angle subtended by the Iris-Pupil Plane with respect to the horizontal axis $\hat{x}$, and where $\tan \xi_v$ is the angle subtended by the Iris-Pupil Plane with respect to the vertical axis $\hat{y}$, and $\alpha$ is the meridian angle regarding to the horizontal (shown in FIG. 3).

It will be appreciated by designers of compact electronic devices such as NED devices that computational efficiency is a major impactor of the computing and power resources that are consumed to implement various eye tracking techniques. To illustrate this point, note that the sampling frequency (Hz) of an eye tracking system refers the number of times per second that discrete positions and/or orientations of the eyes are calculated. As some eye tracking sampling frequencies can range from 60 Hz or lower to even 1200 Hz or more, it is apparent that reducing the computational cost of calculating a single sample measurement yields incremental benefits that continue to increase with increases in the sampling frequency. Thus, mathematical simplifications to eye tracking problems and methodologies can substantially reduce the computing resources consumed to implement eye tracking techniques.

To obtain such computational benefits using the mathematical framework described herein, the geometry of the analytical solution outlined above can be simplified by considering the radius of the iris $p_i$ to be a "known value." For example, the geometry of the analytical solution outlined above can be simplified into a 2D problem based on the points from the iris and/or the pupil. By choosing a value of 0 for the horizontal meridian $\alpha=0$ and also considering the radius of the iris $p_i$ to be a predetermined presumed iris diameter as described above, then a two-equation system (each equation having at least some common variables to the other) can be defined as follows in Equation 13 below:

$$\begin{cases} \left\| t_M(p)\hat{T}_{od}^M(p) - t_c\hat{T}_c \right\| = \left\| \left( \frac{d_c + p_p\tan\xi_h}{\hat{T}_{od}^M(p)\cdot\hat{z}} \right)\hat{T}_{od}^M(p) - \frac{d_c}{\hat{T}_c\cdot\hat{z}}\hat{T}_c \right\| = p_p \\ \left\| t_m(i)\hat{T}_{od}^M(i) - t_c\hat{T}_c \right\| = \left\| \left( \frac{d_c + p_i\tan\xi_h}{\hat{T}_{od}^M(i)\cdot\hat{z}} \right)\hat{T}_{od}^M(p) - \frac{d_c}{\hat{T}_c\cdot\hat{z}}\hat{T}_c \right\| = p_i \end{cases} \quad (13)$$

In the foregoing simplified model, the selection of the value of 0 for the horizontal meridian $\alpha=0$ is not random in nature but rather is due to the specific geometry of the eye.

Figure 16:
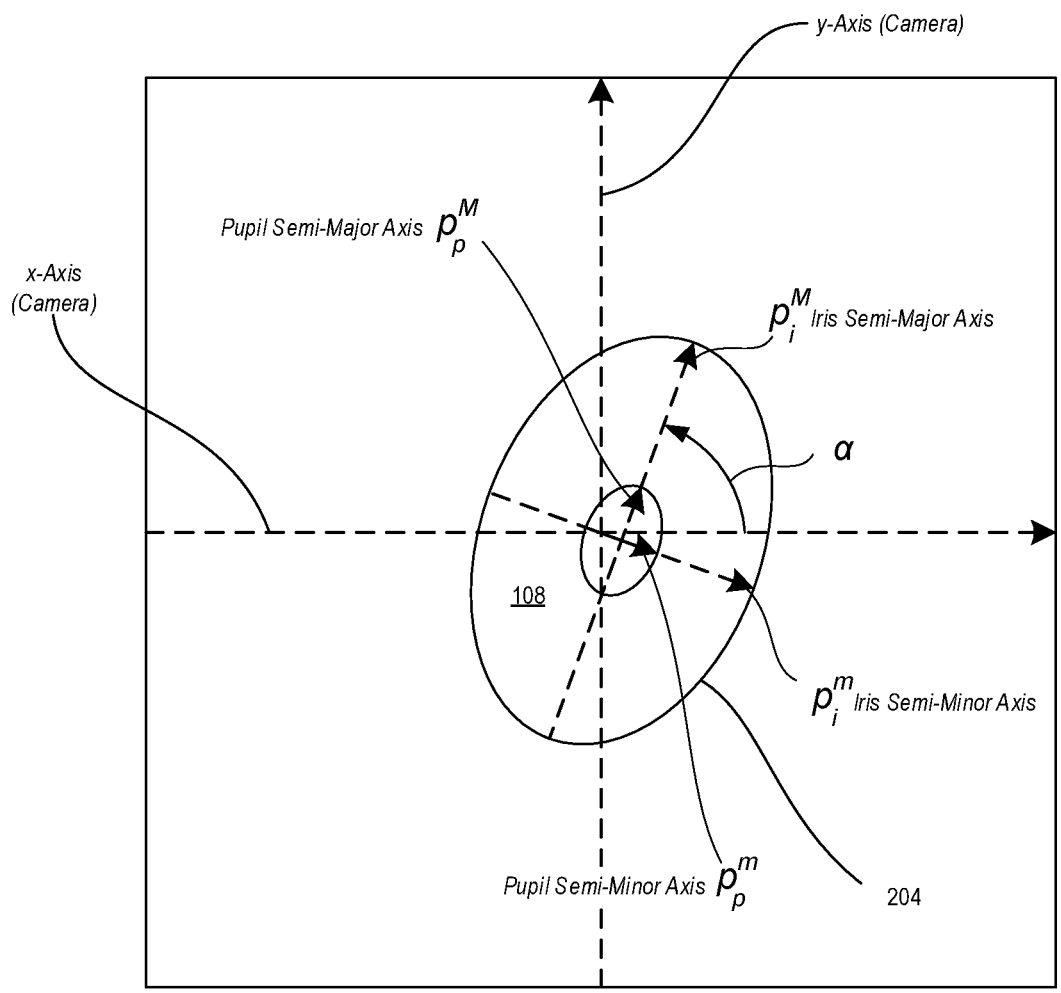
FIG. 16 illustrates a schematic diagram of ellipses captured by a camera to define positional relationships between the iris and the pupil for a particular meridian angle.

Turning now to FIG. 16, illustrated is a schematic diagram of ellipses captured by the camera to define positional relationships between the iris and the pupil for a particular meridian angle. As shown in FIG. 16, the schematic diagram shows linear and angular relationships between the distances of the center of the iris and the center of the ellipse and the distance from the center to the pupil position for that specific meridian. Referring back to equation 13, the pupil radius $p_p$ can be readily calculated using the ellipses that are captured by the camera based on the relationship between the distances of the center of the iris and the center of the ellipse and the distance from the center to the pupil position for that specific meridian (shown in FIG. 16). Then, referring back to FIGS. 14 and 15, the angle $\xi_v$ may be calculated by solving for the perpendicular meridian as outlined below in Equation 14.

$$\left\| t_m \hat{T}_{od}(p) - t_c \hat{T}_c \right\| = \left\| \left( \frac{d_c + p_p \tan \xi_v}{\hat{T}_{od}^m(p) \cdot \hat{z}} \right) \hat{T}_{od}(p) - \frac{d_c}{\hat{T}_c \cdot \hat{z}} \hat{T}_c \right\| = p_p \quad (14)$$

It will be appreciated that the angle $\xi_h$ may be similarly calculated in a similar manner to as described above with respect to the angle $\xi_v$. Once the projected distance onto the $\hat{z}$ axis of the translation $\hat{T}_c$ of the center of the ellipse (i.e. $d_c$) and each of the angles and n of the Iris-Pupil Plane with respect to the reference plane have been calculated, then the orientation of the Iris-Pupil Plane can be evaluated by projecting the points $\vec{r}_M$, $\vec{r}_m$, and $\vec{r}_c$, outward by the previously calculated distances $t_M$, $t_m$, and $t_c$. These projections are represented below in equation 15.

$$\begin{cases} \vec{r}_M = \vec{r}_o + t_M(p)\hat{T}_{od}^M(p) \\ \vec{r}_m = \vec{r}_o + t_m(p)\hat{T}_{od}^m(p) \\ \vec{r}_c = \vec{r}_o + t_c \hat{T}_c \end{cases} \quad (15)$$

Based on the foregoing, it will be appreciated that the respective position in 3D space of $\vec{r}_c$ for each individual eye will determine the dynamic interpupillary distance between the user's eyes. Furthermore, referring back now to the specific geometry illustrated in FIG. 15, the Pupillary axis $\hat{N}_p$ can be obtained as the cross product of the normalized vectors $\hat{N}_{Mc}$ and $\hat{N}_{mc}$. More specifically, the Iris-Pupil Plane characteristic vector (e.g., Pupillary axis) $\hat{N}_p$ can be calculated in real-time as $\hat{N}_p = \hat{N}_{Mc} \times \hat{N}_{mc}$ based on equation 16 shown below:

$$\begin{cases} \hat{N}_{Mc} = \dfrac{\vec{r}_M - \vec{r}_c}{\|\vec{r}_M - \vec{r}_c\|} \\ \hat{N}_{mc} = \dfrac{\vec{r}_m - \vec{r}_c}{\|\vec{r}_m - \vec{r}_c\|} \end{cases} \quad (16)$$

In this way, by use of the predetermined presumed iris diameter, the foregoing analytical solution provides a computationally efficient manner to generating real-time solutions to the novel mathematical framework described in relation to FIGS. 1-13. For example, this analytical solution is fast to solve since it enables calculation of the vergence using only measured values, e.g., the semi-major meridian, the semi-minor axis, and the center of the ellipse.

In some embodiments, the novel mathematical framework described above in relation to FIGS. 1-13 can be solved by comparing measured values to a pre-generated lookup table. During this comparison, the particular lookup table entries that produce the minimum error with respect to the measured values are selected as representing the current eye tracking parameters (e.g., gaze direction, etc.) of the user. In this way, the real-time calculations that are performed to implement the lookup-table-based eye tracking solution may be limited to simple error minimization techniques—thereby providing substantial computational efficiency benefits.

With respect to generating a suitable lookup table, consider that the above description clearly outlines that the ellipses received at the camera sensors will produce a unique pattern of characteristics that include eccentricity, angle, and center coordinates. Further consider that these unique patterns of characteristics depend on the orientation of the Iris-Pupil Plane with respect to the camera plane and also the distance of the Iris-Pupil Plane to the camera plane. Thus, using an anatomical eye model (e.g., the Gullstrand model, the Arizona model, the Liou-Brennan model, and/or the Navarro model) as shown in FIG. 10, it is possible to produce both orientation and spatial position of Iris-Pupil Plane with respect to the sensor plane for a camera that is modeled within the novel mathematical framework described above in relation to FIGS. 1-13. Based on these observations, it is possible to use of an anatomical eye model in conjunction with camera model for producing the lookup table. As described in more detail below, the inputs of the lookup table may be measured parameters of the mathematical framework and the outputs of the table may be modeled parameters of the mathematical framework. As a specific example, the inputs may be the eccentricity and center points of the measured ellipses. Then, upon selecting the most closely matching lookup table values via error minimization, the outputs may be the orientation optical and/or visual axis of the eyes in addition to the dynamic positions of the pupils.

In some embodiments, the camera model may be generated in a suitable mathematical modeling program (e.g., MATLAB by MATHWORKS) based on the nominal (or true) physical dimensions of the cameras with respect to each other and/or a common reference frame. The chosen anatomical eye model may also be generated in the mathematical modeling program to define a spatial relationship between the modeled cameras and the corresponding modeled eye. An exemplary such "camera-eye model" is illustrated in FIGS. 2 and 11 as described above.

Figure 17:
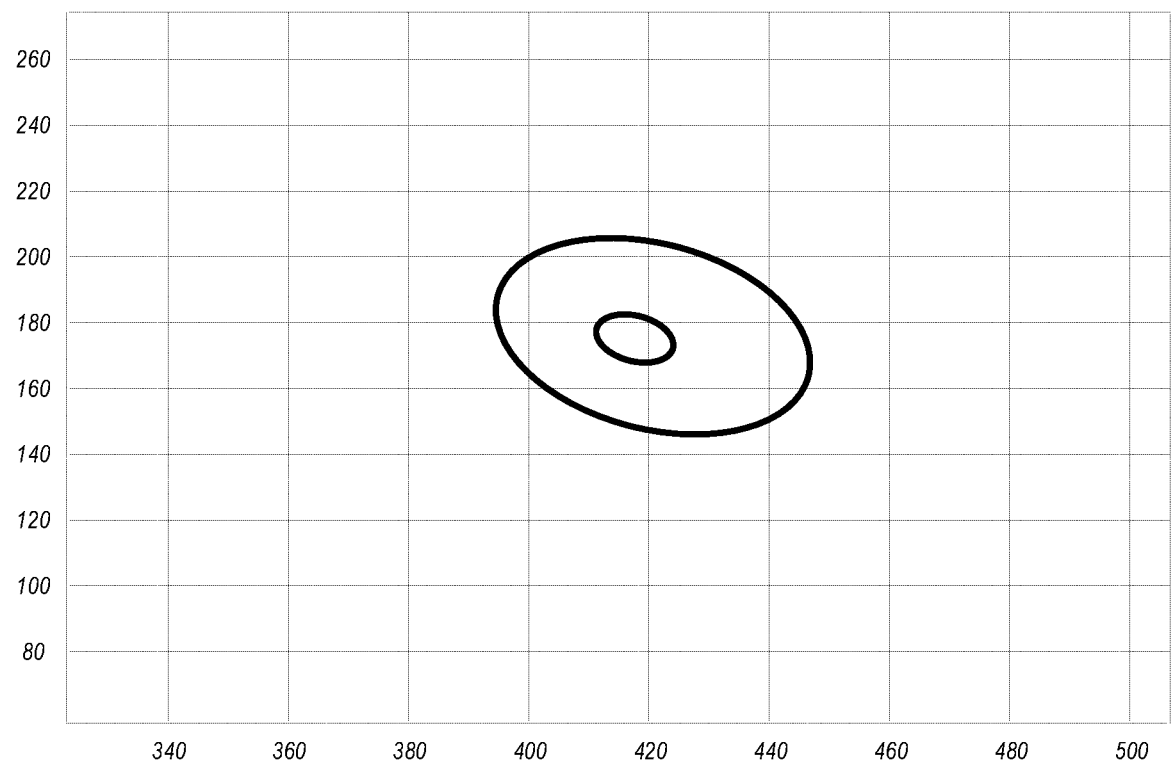
FIG. 17 illustrates exemplary modeled sensor data that is generated within a "camera-eye model" by modeling propagations of rays from a modeled iris and/or pupil of the anatomical eye model onto the modeled sensor plane.

Once the camera-eye model is established, then a plurality of different geometric propagations may be produced—each of which take into account the rays that are launched from the modeled contours of the iris and/or pupil through corresponding predetermined points (e.g., P1 and P2 shown in FIG. 1). For example, the first predetermined point P1 may correspond to a center of an entrance pupil of the first sensor 102(1) whereas the second predetermined point P2 may correspond to a center of an entrance pupil of the second sensor 102(2). The rays reach the camera sensor were their positions are transformed onto pixels with the result being a discretized ellipse as shown in FIG. 17. In particular, FIG. 17 illustrates exemplary modeled sensor data that is generated within a "camera-eye model" by modeling propagations of rays from a modeled iris and/or pupil of the anatomical eye model onto the modeled sensor plane. In FIG. 17, the outer ellipse of the modeled sensor data represents modeled propagations from the iris whereas the inner ellipse of the modeled sensor data represents modeled propagations from the pupil.

Figure 18:
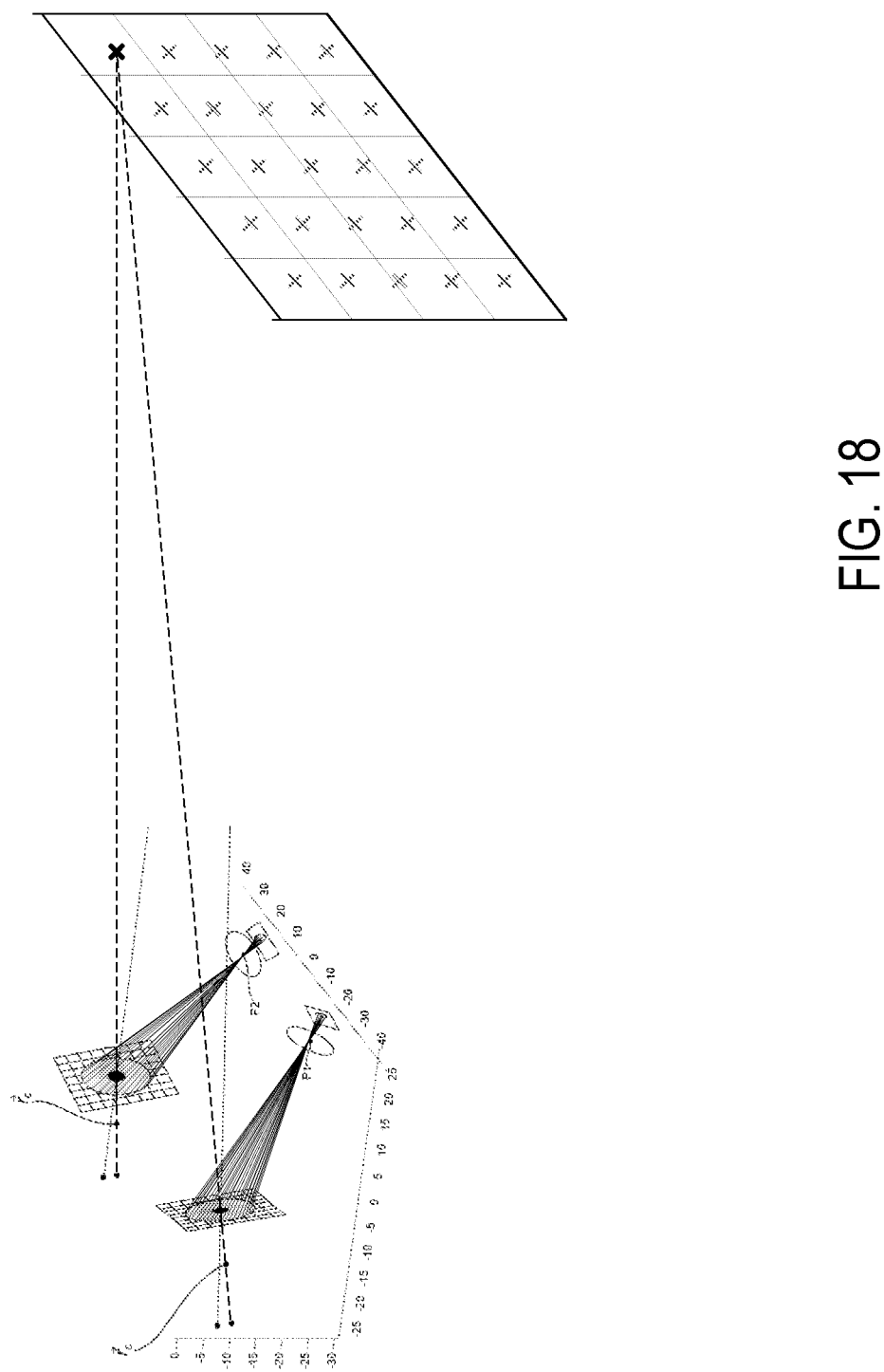
FIG. 18 illustrates an exemplary "camera-eye model" in which propagations from the modeled iris are generated to the sensor plane at a plurality of different modeled eye orientations to generate a lookup table.

Turning now to FIG. 18, illustrated is an exemplary "camera-eye model" in which propagations from the modeled iris are generated to the sensor plane at a plurality of different modeled eye orientations. In particular, in FIG. 18 each of two anatomical eye models are shown to be directing an optical and/or visual axis toward a currently activated one of a plurality of virtual targets. In the illustrated embodiment, there are a total of 25 virtual targets with only a single one being activated. The result of the modeled propagations shown in FIG. 18 may be the modeled sensor data as shown in FIG. 17. This process is repeated for each of the different virtual targets to generate an individual instance of the modeled sensor data for each individual virtual target.

Figure 19:
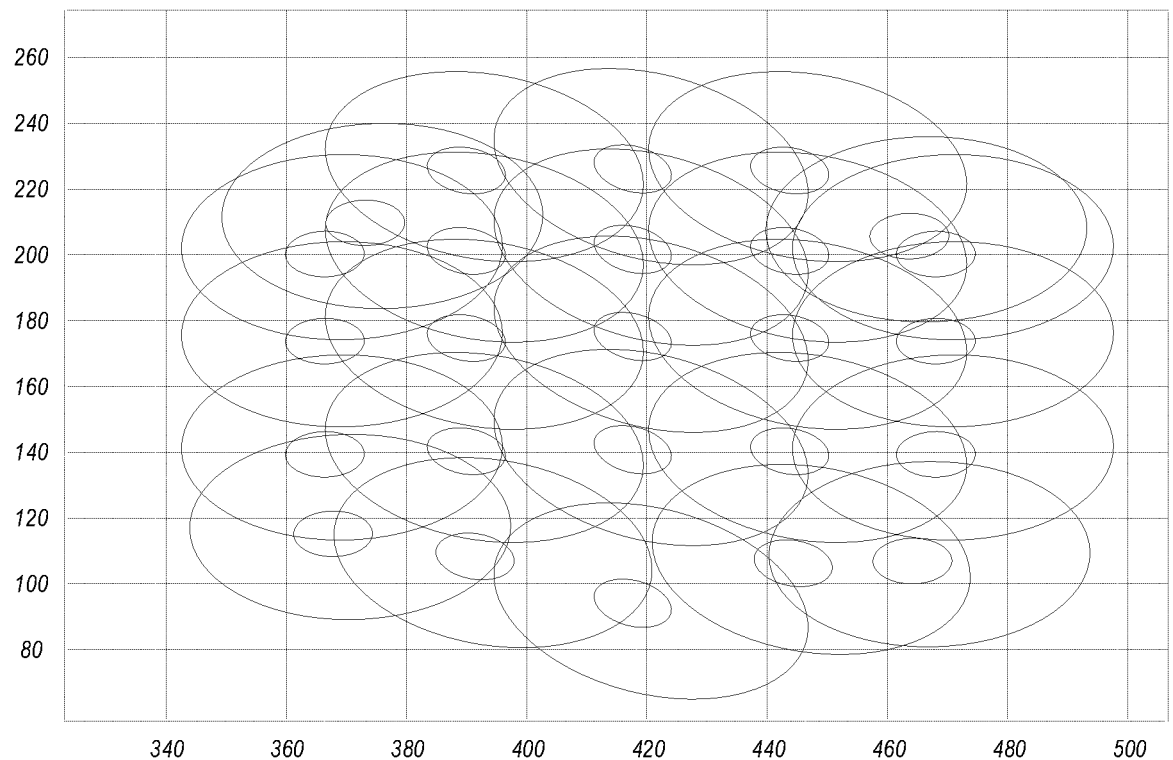
FIG. 19 illustrates an exemplary aggregation of modeled sensor data that corresponds to a lookup table generated via the "camera-eye model" described herein.

Turning now to FIG. 19, illustrated is an exemplary aggregation of modeled sensor data that corresponds to a lookup table generated via the "camera-eye model" described herein. The exemplary aggregation of modeled sensor data includes an instance of the modeled sensor data that uniquely corresponds to each individual virtual target as shown in FIG. 18. That is, each individual one of the many overlapping instances of modeled sensor data represent what measured sensor data is likely to closely resemble in terms of ellipticity parameters and center location under circumstances where a real user's optical and/or visual axis (whichever is used for modeling purposes to generate the lookup table) is oriented and positioned as modeled to generate the modeled sensor data. Stated plainly, the lookup table represents a modeled sensor data that is generated to cover a plurality of different sensor-to-eye spatial relationships (e.g., positional relationships in terms of both location and orientation).

Once the lookup table has been fully generated, then during operation the real sensors may be used to generate instances of eye tracking data in the form of pixel data that defines an image of circular feature(s) of the user's eyes. As described above, the pixel data may include elliptical representations of the circular features of the eyes. These elliptical representations may provide the "measured" inputs to the lookup table which may be, for example, the eccentricity and center points of the measured ellipses. Based on these inputs, error minimization techniques may be performed to determine which generated instance of modeled sensor data most closely matches the inputs that are actually measured via the real sensors. Then, upon selecting the most closely matching lookup table values, the outputs of the lookup table are retrieved—the outputs being previously modeled during generation of the lookup table. Exemplary lookup table outputs may include, but are not limited to, eccentricity, center position, tilting angle, the orientation optical and/or visual axis of the eyes, and/or the dynamic positions of the pupils.

In some embodiments, the appropriate instance of modeled sensor data from the lookup table may be selected based on a neighborhood algorithm. Such an algorithm is a relatively simple solution that can be performed very quickly—depending on the density of the sample. Using this algorithm, once the ellipse output values are calculated and included in the lookup table, then the closest matching values to the eye tracking data obtained during operation are found in near real time as the minimum square Error or minimum square Euclidean distance from the calculated values $\{x(i), y(i), \alpha(i), ecc(i)\}$—with the new inputs $\{x_0, y_0, \alpha_0, ecc\alpha_0\}$ being usable in Equation 17 shown below.

$$Err(i) = \left[1 - \frac{x(i)}{x_0}\right]^2 + \left[1 - \frac{y(i)}{y_0}\right]^2 + \left[1 - \frac{\alpha(i)}{\alpha_0}\right]^2 + \left[1 - \frac{ecc(i)}{ecc_0}\right]^2 \quad (17)$$

It will be appreciated that the outcome of this algorithm is not only the distance of the pupil regarding to the camera, but also the optical axis.

In some embodiments, the appropriate instance of modeled sensor data from the lookup table may be selected based on an interpolation algorithm. Such an algorithm may provide benefits of increased accuracy while also providing for such accurate results via the user of lookup tables with smaller samples modeled therein. Exemplary interpolation algorithms include, but are not limited to, Delaunay decomposition, barycentric coordinates, and so on.

In some embodiments, the novel mathematical framework described above in relation to FIGS. 1-13 can be solved using a minimization solution to calculate the intersection points of the projected camera with a discrete number of planes. The first the previous two solutions (i.e., the analytical solution) described Equation 12. An examination of Equation 12 above reveals that it includes 3 variables and that 2 of these variable are separable on one side we have the distance d and on the other the angular variables $\{\xi_h, \xi_v\}$ that denote the rotations from the world horizontal and vertical axes. These variables when expressed in spherical coordinates on terms of the azimuth $\phi$ and elevation $\theta$ of the eye regarding to the world coordinates produce the characteristic vector $\hat{N}_p$ that is defined below in Equation 18. This reveals a minimization solution that can be completed in two steps. The first step is to identify the plane that shows the minimum eccentricity and to use the identified plane to find the distance where the eccentricity is minimum.

In order to find the plane, we did consider biological constrictions imposed by the eye. In particular, it is presumed that the planes can be oriented only in within a range for elevation from 0 to 25 deg. The different planes are characterized by the normal vector expressed in spherical coordinates:

$$\hat{N}_p = \{\cos\phi \cdot \sin\Theta, \sin\phi \cdot \sin\Theta, \cos\Theta\} \quad (18)$$

with $\phi \in [0, 2\pi]$ and $\Theta \in$ $$\left[0, \frac{\pi}{6}\right]$$

Then, the intersection points of the projected 3D points from the sensor to the planes $\vec{r}_p = \vec{r}_o + t\hat{T}_{od}$ can be calculated from the traveling distance t from the origin $\vec{r}_o$ of the point to the intersection of the plane described in equation 18 as Equation 19.

$$t = t_c \frac{\hat{T}_c \hat{N}_p}{\hat{T}_{od} \hat{N}_p} \quad (19)$$

where $\hat{T}_c$ is the propagation vector of the center of the ellipse, and $t_c$ is an arbitrary distance that will be calculated in the second of these two steps. The error function picked for minimization is the square of the eccentricity, since the pupil is less elliptical when it is projected onto the right plane Equation 20.

$$Err(\Theta, \phi) = \frac{\left\|\vec{r}_d^M(\Theta, \phi) - \vec{r}_d^C(\Theta, \phi)\right\|^2}{\left\|\vec{r}_d^m(\Theta, \phi) - \vec{r}_d^C(\Theta, \phi)\right\|^2} - 1 \quad (20)$$

where $\vec{r}_d^M (\Theta, \phi)$, and $\vec{r}_d^m (\Theta, \phi)$ are the Maximum and minimum radii in the plane.

The foregoing complete solutions to the novel mathematical framework described above in relation to FIGS. 1-13 are provided as examples only. It will be appreciated that other complete solutions exist and are within the scope of the present disclosure.

Figure 20:
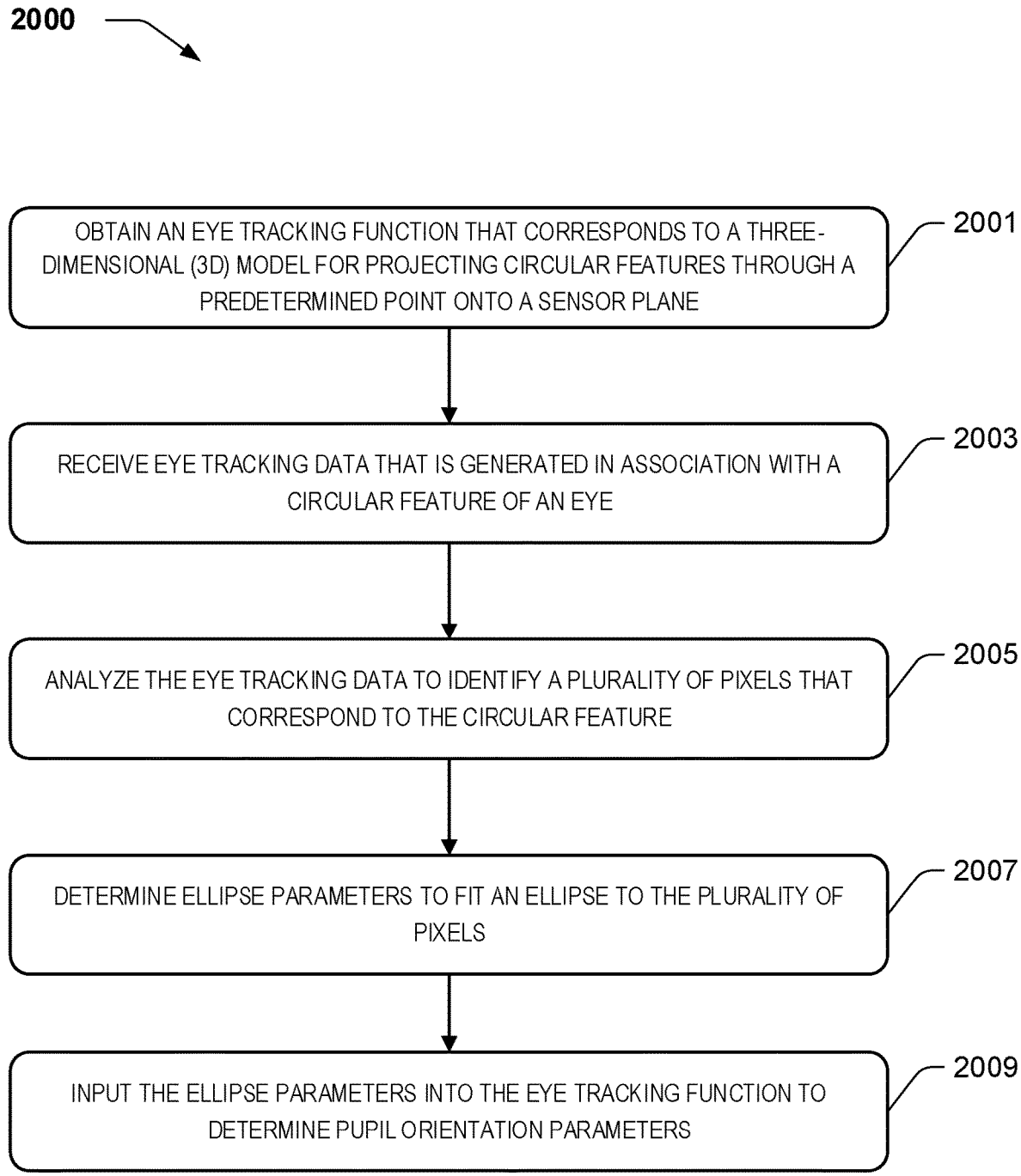
FIG. 20 is a flow diagram of a process to use an eye tracking function that corresponds to a three-dimensional (3D) model for projecting "circular" features through a predetermined point onto a sensor plane.

Turning now to FIG. 20, a flow diagram is illustrated of a process 2000 to use an eye tracking function that corresponds to a three-dimensional (3D) model for projecting "circular" features through a predetermined point onto a sensor plane. As described above, the "circular" features may reside on an Iris-Pupil Plane that is angularly offset from the sensor plane such that the "circular" features appear elliptical from the perspective of the sensor.

At block 2001, a system (e.g., the NED device 100) may obtains an eye tracking function. The eye tracking function may correspond to various complete solutions to the novel mathematical framework described above. For example, the eye tracking function may correspond to the analytical solution described above which is usable to determine pupil orientation parameters that include Iris-Pupil Plane characteristic vectors that are individually calculated based, at least in part, on predetermined presumed iris diameter. As another example, the eye tracking function may correspond to a lookup table that is pre-generated (i.e., generated prior to the process 2000 being implemented to perform real-time eye tracking) via the "camera-eye model" that is described herein.

At block 2003, the system may receive eye tracking data that is generated in association with at least one circular feature of at least one eye of a user. As described above, the eye tracking data may be in the form of pixel data that defines pixel values that form an image of the at least one eye of the user.

At block 2005, the system may analyze the eye tracking data to identify a plurality of pixels that correspond to the circular feature. For example, the pixels representing the pupil contour (e.g., as shown in FIGS. 5A and 5B) may be isolated from the rest of the eye.

At block 2007, the system may determine ellipse parameters to fit an ellipse to the plurality of pixels. For example, the pixels representing the pupil contour that may be isolated at block 2005, may be fitted to a tilted ellipse. As a specific but non-limiting example, the isolated pupil contour may then be fitted to a tilted ellipse using a least square algorithm.

At block 2009, the system may input the ellipse parameters into the eye tracking function to determine pupil orientation parameters of the at least one eye of the user. In some embodiments, as described in relation to FIG. 19 above, inputting the ellipse parameters into the eye tracking function includes selecting generated instances of modeled sensor data based on a degree to which these instances match the ellipse parameters. In some other embodiments, as described above in relation to FIGS. 14-15, inputting the ellipse parameters into the eye tracking function outputs may yield outputs of Iris-Pupil Plane characteristic vectors that are determined based on projections of the isolated pixels through a predetermined point in front of a sensor plane.

Example Clauses

Example Clause A, a computer-implemented method, comprising: obtaining an eye tracking function that corresponds to a three-dimensional (3D) model for projecting individual circular features through at least one of a first predetermined point onto a first sensor plane, or a second predetermined point onto a second sensor plane; receiving, from at least one sensor, pixel data that is generated in association with a first circular feature of a first eye of a user and a second circular feature of a second eye of the user; analyzing the pixel data to identify a first plurality of pixels that correspond to the first circular feature and a second plurality of pixels that correspond to the second circular feature; determining first ellipse parameters to fit a first ellipse to the first plurality of pixels and second ellipse parameters to fit a second ellipse to the second plurality of pixels; and inputting the first ellipse parameters and the second ellipse parameters into the eye tracking function to determine pupil orientation parameters that define a spatial-angular relationship between the first eye and the second eye.

Example Clause B, the computer-implemented method of Example Clause A, wherein the eye tracking function outputs the pupil orientation parameters based, at least in part, on predetermined presumed iris diameter.

Example Clause C, the computer-implemented method of any one of Example Clauses A through B, wherein the pupil orientation parameters include at least a first Iris-Pupil Plane characteristic vector and second Iris-Pupil Plane characteristic vector.

Example Clause D, the computer-implemented method of any one of Example Clauses A through C, wherein the first Iris-Pupil Plane characteristic vector is determined by cross multiplying first normalized vectors of the first eye, and wherein the second Iris-Pupil Plane characteristic vector is determined by cross multiplying second normalized vectors of the second eye.

Example Clause E, the computer-implemented method of any one of Example Clauses A through D, wherein the inputting the first ellipse parameters and the second ellipse parameters into the eye tracking function outputs: a first Iris-Pupil Plane characteristic vector that is determined based on projections of the first plurality of pixels through a first predetermined point in front of the first sensor plane, and a second Iris-Pupil Plane characteristic vector that is determined based on projections of the second plurality of pixels through a second predetermined point in front of the second sensor plane.

Example Clause F, the computer-implemented method of any one of Example Clauses A through E, wherein the eye tracking function corresponds to a lookup table that is generated based on a plurality of instances of modeled sensor data, individual instances of the modeled sensor data uniquely corresponding to individual virtual targets of a camera-eye model.

Example Clause G, the computer-implemented method of any one of Example Clauses A through F, wherein the pupil orientation parameters are determined by selecting particular instances of the modeled sensor data that match the first ellipse parameters and the second ellipse parameters to a greater degree than other generated instances of the modeled sensor data.

Example Clause H, the computer-implemented method of any one of Example Clauses A through G, wherein the pupil orientation parameters define an interpupillary distance between the first eye and the second eye.

Example Clause I, a Near-Eye-Display (NED) system, comprising: a sensor configured to generate eye tracking data associated with at least one substantially circular feature of an eye of a user; a controller that is communicatively coupled to the sensor, wherein the controller is configured to perform operations that include: receiving the eye tracking data from the sensor, wherein the eye tracking data defines pixel values that form an image of the eye on a sensor plane of the sensor; analyzing the pixel values that form the image of the eye to isolate a plurality of pixels that correspond to the at least one substantially circular feature of the eye; determining ellipse parameters associated with at least one ellipse that is fitted to the plurality of pixels; and inputting the ellipse parameters into an eye tracking function to determine pupil orientation parameters that define a spatial-angular relationship between the eye and the sensor.

Example Clause J, the NED device of Example Clause I, wherein the inputting the ellipse parameters into the eye tracking function includes selecting at least one generated instance of modeled sensor data that matches the at least one ellipse, that is fitted to the plurality of pixels, to a greater degree than other generated instances of the modeled sensor data.

Example Clause K, the NED device of any one of Example Clauses I through J, wherein the selecting the at least one generated instance of the modeled sensor data includes selecting the at least one generated instance from a lookup table based on at least one of: a neighborhood algorithm, or an interpolation algorithm.

Example Clause L, the NED device of any one of Example Clauses I through K, wherein the pupil orientation parameters define an Iris-Pupil Plane characteristic vector that is determined within the eye tracking function by cross multiplying at least two normalized vectors of the eye.

Example Clause M, the NED device of any one of Example Clauses I through L, wherein the at least two normalized vectors are calculated based on projections of individual pixels of the plurality of pixels that correspond to the at least one substantially circular feature of the eye, the projections extending from the sensor plane through a predetermined point in front of the sensor plane.

Example Clause N, the NED device of any one of Example Clauses I through M, wherein the eye tracking function outputs the pupil orientation parameters based, at least in part, on a predetermined presumed iris diameter.

Example Clause O, the NED device of any one of Example Clauses I through N, wherein the pupil orientation parameters define at least one of an optical axis of the eye with respect to the sensor, or a visual axis of the eye with respect to the sensor.

Example Clause P, the NED device of any one of Example Clauses I through O, wherein the eye tracking function corresponds to a three-dimensional (3D) model for projecting individual circular features through an entrance pupil of the sensor onto the sensor plane.

Example Clause Q, an eye tracking system, comprising: at least one sensor to configured to generate eye tracking data that defines pixel values that form an image; at least one processor; and at least one memory in communication with the at least one processor, the at least one memory having computer-readable instructions stored thereupon that, when executed by the at least one processor, cause the at least one processor to: receive the eye tracking data from the sensor; analyzing the pixel values to isolate a plurality of pixels that correspond to at least one substantially circular feature of an eye of a user; determining ellipse parameters associated with at least one ellipse that is fitted to the plurality of pixels; and inputting the ellipse parameters into an eye tracking function to determine pupil orientation parameters that define a spatial-angular relationship between the at least one eye and the at least one sensor.

Example Clause R, the eye tracking system of Example Clause Q, wherein the pupil orientation parameters are determined by selecting particular instances of modeled sensor based on a degree to which the particular instances of the modeled sensor data match the ellipse parameters associated with at least one ellipse that is fitted to the plurality of pixels.

Example Clause S, the eye tracking system of any one Example Clauses Q through R, wherein the pupil orientation parameters include at least one Iris-Pupil Plane characteristic vector that is determined based, at least in part, on predetermined presumed iris diameter.

Example Clause T, the eye tracking system of any one Example Clauses Q through S, wherein the at least one Iris-Pupil Plane characteristic vector is determined within the eye tracking function by cross multiplying at least two normalized vectors of the at least one eye.

Conclusion

In closing, although the various techniques have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

What is claimed is:

1. A computer-implemented method, comprising:
    obtaining an eye tracking function that corresponds to a three-dimensional (3D) model for projecting individual circular features through a first predetermined point onto a first sensor plane, or a second predetermined point onto a second sensor plane;
    receiving, from at least one sensor, pixel data that is generated in association with a first circular feature of a first eye of a user, and a second circular feature of a second eye of the user;
    identifying, based on the pixel data, a first plurality of pixels that correspond to the first circular feature, and a second plurality of pixels that correspond to the second circular feature;
    determining first ellipse parameters that fit a first ellipse to the first plurality of pixels and second ellipse parameters that fit a second ellipse to the second plurality of pixels; and
    generating, based on the eye tracking function, propagation data that defines a first set of lines extending from the first ellipse through the first predetermined point, and a second set of lines extending from the second ellipse through the second predetermined point; and
    determine, based on the propagation data, pupil orientation parameters that define a spatial-angular relationship between the first eye and the second eye.

2. The computer-implemented method of claim 1, wherein the eye tracking function outputs the pupil orientation parameters based, at least in part, on a predetermined presumed iris diameter.

3. The computer-implemented method of claim 1, wherein the pupil orientation parameters include at least a first Iris-Pupil Plane characteristic vector and second Iris-Pupil Plane characteristic vector.

4. The computer-implemented method of claim 3, wherein the first Iris-Pupil Plane characteristic vector is determined by cross multiplying first normalized vectors of the first eye, and wherein the second Iris-Pupil Plane characteristic vector is determined by cross multiplying second normalized vectors of the second eye.

5. The computer-implemented method of claim 1, wherein the inputting the first ellipse parameters and the second ellipse parameters into the eye tracking function outputs:
a first Iris-Pupil Plane characteristic vector that is determined based on projections of the first plurality of pixels through a first predetermined point in front of the first sensor plane, and
a second Iris-Pupil Plane characteristic vector that is determined based on projections of the second plurality of pixels through a second predetermined point in front of the second sensor plane.

6. The computer-implemented method of claim 1, wherein the eye tracking function corresponds to a lookup table that is generated based on a plurality of instances of modeled sensor data, individual instances of the modeled sensor data uniquely corresponding to individual virtual targets of a camera-eye model.

7. The computer-implemented method of claim 6, wherein the pupil orientation parameters are determined by selecting particular instances of the modeled sensor data that match the first ellipse parameters and the second ellipse parameters to a greater degree than other generated instances of the modeled sensor data.

8. The computer-implemented method of claim 1, wherein the pupil orientation parameters define an interpupillary distance between the first eye and the second eye.

9. A Near-Eye-Display (NED) system, comprising:
a sensor configured to generate eye tracking data associated with at least one substantially circular feature of an eye of a user;
a controller that is communicatively coupled to the sensor, wherein the controller is configured to perform operations that include:
receiving the eye tracking data from the sensor, wherein the eye tracking data defines pixel values that form an image of the eye on a sensor plane of the sensor;
analyzing the pixel values that form the image of the eye to isolate a plurality of pixels that correspond to the at least one substantially circular feature of the eye;
determining ellipse parameters associated with at least one ellipse that is fitted to the plurality of pixels; and
generating, based on an eye tracking function, propagation data that defines one or more lines extending from the at least one ellipse through a predetermined point; and
determine, based on the propagation data, pupil orientation parameters that define a spatial-angular relationship between the eye and the sensor.

10. The NED device of claim 9, wherein the operations further include selecting at least one generated instance of modeled sensor data that matches the at least one ellipse, that is fitted to the plurality of pixels, to a greater degree than other generated instances of the modeled sensor data.

11. The NED device of claim 10, wherein the selecting the at least one generated instance of the modeled sensor data includes selecting the at least one generated instance from a lookup table based on at least one of: a neighborhood algorithm, or an interpolation algorithm.

12. The NED device of claim 9, wherein the pupil orientation parameters define an Iris-Pupil Plane characteristic vector that is determined within the eye tracking function by cross multiplying at least two normalized vectors of the eye.

13. The NED device of claim 12, wherein the at least two normalized vectors are calculated based on projections of individual pixels of the plurality of pixels that correspond to the at least one substantially circular feature of the eye, the projections extending from the sensor plane through a predetermined point in front of the sensor plane.

14. The NED device of claim 9, wherein the eye tracking function outputs the pupil orientation parameters based, at least in part, on a predetermined presumed iris diameter.

15. The NED device of claim 9, wherein the pupil orientation parameters define at least one of an optical axis of the eye with respect to the sensor, or a visual axis of the eye with respect to the sensor.

16. The NED device of claim 9, wherein the eye tracking function corresponds to a three-dimensional (3D) model for projecting individual circular features through an entrance pupil of the sensor onto the sensor plane.

17. An eye tracking system, comprising:
at least one sensor configured to generate eye tracking data that defines pixel values that form an image;
at least one processor; and
at least one memory in communication with the at least one processor, the at least one memory having computer-readable instructions stored thereupon that, when executed by the at least one processor, cause the at least one processor to:
receive the eye tracking data from the sensor;
analyze the pixel values to isolate a plurality of pixels that correspond to at least one substantially circular feature of an eye of a user;
determine ellipse parameters associated with at least one ellipse that is fitted to the plurality of pixels;
input the ellipse parameters into an eye tracking function to generate propagation data that defines at least one set of lines extending from the at least one ellipse through a predetermined point; and
determine, based on the propagation data, pupil orientation parameters that define a spatial-angular relationship between the at least one eye and the at least one sensor.

18. The eye tracking system of claim 17, wherein the pupil orientation parameters are determined by selecting particular instances of modeled sensor data based on a degree to which the particular instances of the modeled sensor data match the ellipse parameters associated with at least one ellipse that is fitted to the plurality of pixels.

19. The eye tracking system of claim 17, wherein the pupil orientation parameters include at least one Iris-Pupil Plane characteristic vector that is determined based, at least in part, on predetermined presumed iris diameter.

20. The eye tracking system of claim 19, wherein the at least one Iris-Pupil Plane characteristic vector is determined within the eye tracking function by cross multiplying at least two normalized vectors of the at least one eye.

* * * * *

UNITED STATES PATENT AND TRADEMARK OFFICE
CERTIFICATE OF CORRECTION

Page 1 of 1

PATENT NO. : 10,996,746 B2
APPLICATION NO. : 16/414637
DATED : May 4, 2021
INVENTOR(S) : Sergio Ortiz Egea et al.

It is certified that error appears in the above-identified patent and that said Letters Patent is hereby corrected as shown below:

On the Title Page

Column 1, (72), Inventors Section please delete:
"(Redmond, WA)" from Gao; Jian Feng
And insert:
--(Cupertino, CA)--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*